US006790835B1

(12) United States Patent
Qiu et al.

(10) Patent No.: US 6,790,835 B1
(45) Date of Patent: Sep. 14, 2004

(54) BICYCLIC MACROLIDE DERIVATIVES

(75) Inventors: Yao-Ling Qiu, Andover, MA (US); Ly Tam Phan, Malden, MA (US); Tongzhu Liu, Auburndale, MA (US); Zhigang Chen, Acton, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 30 days.

(21) Appl. No.: 10/455,219

(22) Filed: Jun. 5, 2003

(51) Int. Cl.$^7$ .................. A61K 31/70; C07H 17/08
(52) U.S. Cl. .................. 514/29; 536/7.2; 536/7.3; 536/7.4
(58) Field of Search .................. 514/29; 536/7.2, 536/7.3, 7.4

(56) References Cited

U.S. PATENT DOCUMENTS

| 5,866,549 A | | 2/1999 | Or et al. ............ 514/29 |
| 6,028,181 A | * | 2/2000 | Or et al. ............ 536/7.2 |
| 6,124,269 A | | 9/2000 | Phan et al. .......... 514/29 |
| 6,399,582 B1 | | 6/2002 | Hlasta et al. ........ 514/29 |

FOREIGN PATENT DOCUMENTS

| WO | WO 97/042205 A1 | 11/1997 | ........ C07H/17/08 |
| WO | WO 02/016380 A1 | 2/2002 | ........ C07H/17/08 |
| WO | WO 02/050091 A1 | 6/2002 | ........ C07H/17/08 |
| WO | WO 02/050092 A1 | 6/2002 | ........ C07H/17/08 |
| WO | WO 03/004509 A2 | 1/2003 | ........ C07H/17/08 |
| WO | WO 03/024986 A1 | 3/2003 | ........ C07H/17/08 |

OTHER PUBLICATIONS

Anhydrolide Macrolides. 1. Synthesis and Antibacterial Activity of 2,3–Anhydro–6–O–methyl 11,12–Carbamate Erythromycin A Analogs, Elliott et al, J. Med. Chem. 1998, 41, 1651–1659.

Anhydrolide Macrolides. 2. Sythesis and Antibacterial Activity of 2,3–Anhydro–6–O–methyl 11,12–Carbazate Erythromycin A Analogs, Griesgraber et al, J. Med. Chem. 1998, 41, 1660–1670.

* cited by examiner

Primary Examiner—Elli Peselev
(74) Attorney, Agent, or Firm—Jason D. Ferrone

(57) ABSTRACT

The present invention discloses compounds of formula I, or pharmaceutically acceptable salts, esters, or prodrugs thereof:

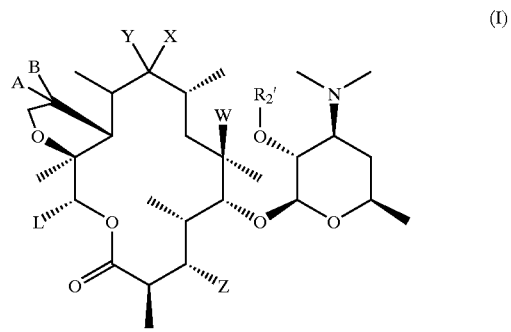

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

9 Claims, No Drawings

BICYCLIC MACROLIDE DERIVATIVES

REFERENCE TO RELATED APPLICATIONS

This application is related to commonly assigned U.S. patent applications, Ser. Nos. 10/455,648, 10/455,001 and 10/454,865, filed on even date herewith.

TECHNICAL FIELD

The present invention relates to novel semisynthetic macrolides having antibacterial activity and which are useful in the treatment and prevention of bacterial infections. More particularly, the invention relates to 11,12-cyclized erythromycin derivatives, compositions containing such compounds and methods for using the same, as well as processes for making such compounds.

BACKGROUND OF THE INVENTION

Erythromycins A through D, represented by formula (E) as illustrated below,

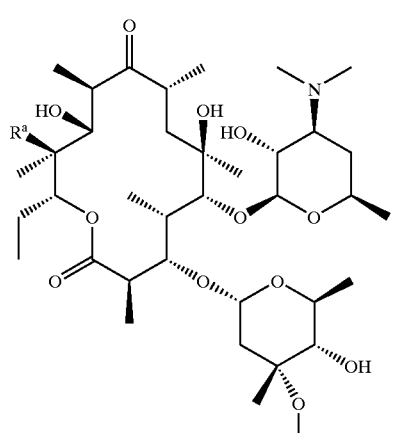

| Erythromycin | $R^a$ | $R^b$ |
|---|---|---|
| A | —OH | —CH$_3$ |
| B | —H | —CH$_3$ |
| C | —OH | —H |
| D | —H | —H | are well-known and potent antibacterial agents, used widely to treat and prevent bacterial infection. As with other antibacterials, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

Kashimura et al. have disclosed 6-O-methylerythromycin derivatives having a tricyclic basic nuclear structure in European Application 559896, published Nov. 11, 1991. Also, Asaka et al. have disclosed 5-O-desoaminylerythronolide derivatives containing a tricyclic carbamate structure in PCT Application WO 93/21200, published Apr. 22, 1992.

Recently erythromycin derivatives containing a variety of substituents at the 6-O position have been disclosed in U.S. Pat. Nos. 5,866,549, 6,075,011 and 6,420,555 B1 as well as PCT Applications WO 00/78773 and WO 03/024986. Furthermore, Ma et. al. have described erythromycin derivatives with aryl groups tethered to the C-6 position in *J. Med Chem.*, 44, pp 4137–4156 (2001).

More recently, erythromycin derivatives containing a lactone moiety at the C11–C12 position have been disclosed in PCT Application WO 02/16380, published Feb. 28, 2002 as well as WO 02/50091 and WO 02/50092, both published Jun. 27, 2002 and WO 03/024986, which published Mar. 27, 2003.

SUMMARY OF THE INVENTION

The present invention provides a novel class of C11–C12 cyclized erythromycin compounds that possess antibacterial activity.

In one aspect of the present invention there are disclosed novel bicyclic erythromycin compounds represented by formula I as illustrated below:

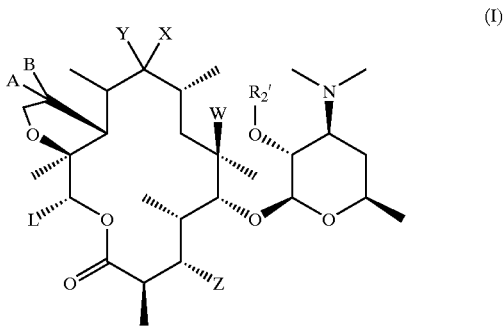

as well as the pharmaceutically acceptable salts, esters and prodrugs thereof.

In formula I:

A is selected from:
  (a) —OH;
  (b) —OR$_p$, where R$_p$ is a hydroxy protecting group;
  (c) —R$_1$, where R$_1$ is selected from:
    1. aryl;
    2. substituted aryl;
    3. heteroaryl; and
    4. substituted heteroaryl;
  (d) —OR$_1$, where R$_1$ is as previously defined;
  (e) —R$_2$, where R$_2$ is selected from:
  (f) hydrogen;
  (g) halogen;
    1. C$_1$–C$_6$ alkyl containing 0, 1, 2, or 3 heteroatoms selected from O, S and N, optionally substituted with one or more substituents selected from halogen, cyano, oxo, aryl, substituted aryl, heteroaryl and substituted heteroaryl;
    2. C$_2$–C$_6$ alkenyl containing 0, 1, 2, or 3 heteroatoms selected from O, S and N, optionally substituted with one or more substituents selected from halogen, cyano, oxo, aryl, substituted aryl, heteroaryl and substituted heteroaryl; and
    3. C$_2$–C$_6$ alkynyl containing 0, 1, 2, or 3 heteroatoms selected from O, S and N, optionally substituted with one or more substituents selected from halogen, cyano, oxo, aryl, substituted aryl, heteroaryl and substituted heteroaryl;
  (h) —OR$_2$, where R$_2$ is previously defined;

(i) —S(O)$_n$R$_{11}$, where n=0, 1 or 2, and R$_{11}$ is selected from hydrogen, R$_1$ and R$_2$, where R$_1$ and R$_2$ are as previously defined
(j) —OC(O)R$_{11}$, where R$_{11}$ is as previously defined;
(k) —C(O)R$_{11}$, where R$_{11}$ is as previously defined;
(l) —C(O)NHR$_{11}$, where R$_{11}$ is as previously defined;
(m) —OC(O)NHR$_{11}$, where R$_{11}$ is as previously defined;
(n) —NHC(O)R$_{11}$, where R$_{11}$ is as previously defined;
(o) —NHC(O)NHR$_{11}$, where R$_{11}$ is as previously defined;
(p) —NHS(O)$_n$R$_{11}$, where n and R$_{11}$ are as previously defined;
(q) —NR$_{14}$R$_{15}$, where R$_{14}$ and R$_{15}$ are each independently R$_{11}$, where R$_{11}$ is as previously defined; and
(r) —NHR$_3$, where R$_3$ is an amino protecting group;

B is selected from:
(a) hydrogen;
(b) deuterium;
(c) —CN;
(d) —NO$_2$;
(e) halogen;
(f) —OH;
(g) —R$_1$, where R$_1$ is as previously defined;
(h) —R$_2$, where R$_2$ is as previously defined; and
(i) —OR$_p$, where R$_p$ is as previously defined;

provided that when B is halogen, —NO$_2$, —OH or OR$_p$, A is R$_1$ or R$_2$;

or, alternatively, A and B taken together with the carbon atom to which they are attached are selected from:
(a) C=O;
(b) C(OR$_2$)$_2$, where R$_2$ is as previously defined;
(c) C(SR$_2$)$_2$, where R$_2$ is as previously defined;
(d) C(OR$_{12}$)(OR$_{13}$), where R$_{12}$ and R$_{13}$ taken together are —(CH$_2$)$_m$—, and where m is 2 or 3;
(e) C(SR$_{12}$)(SR$_{13}$), where R$_{12}$ and R$_{13}$ taken together are —(CH$_2$)$_m$ and, where m is as previously defined,
(f) C=CR$_{11}$R$_{14}$, where R$_{11}$ and R$_{14}$ are as previously defined;
(g) C=N—O—R$_{11}$, where R$_{11}$ is as previously defined;
(h) C=NNHR$_{11}$, where R$_{11}$ is as previously defined;
(i) C=NNHC(O)R$_{11}$, where R$_{11}$ is as previously defined;
(j) C=NN=CR$_{11}$R$_{14}$, where R$_{11}$ and R$_{14}$ are as previously defined;
(k) C=NNHC(O)NHR$_{11}$, where R$_{11}$ is as previously defined;
(l) C=NNHS(O)$_n$R$_{11}$, where n and R$_{11}$ are as previously defined;
(m) C=NNHR$_3$, where R$_3$ is as previously defined; and
(n) C=NR$_{11}$, where R$_{11}$ is as previously defined;

one of X and Y is hydrogen and the other is selected from:
(a) hydrogen;
(b) deuterium;
(c) —OH;
(d) —OR$_p$, where R$_p$ is as previously defined; and
(e) —NR$_4$R$_5$, where R$_4$ and R$_5$ are each independently selected from:
  1. hydrogen; and
  2. C$_1$–C$_{12}$ alkyl, optionally substituted with one or more substituents selected from halogen, cyano, aryl, substituted aryl, heteroaryl and substituted heteroaryl; or R$_4$ and R$_5$, taken together with the nitrogen atom to which they are attached form a 3–10 membered heteroalkyl ring containing 0–2 additional hetero atoms selected from O, S and N; or alternatively, X and Y taken together with the carbon atom to which they are attached are selected from:
(a) C=O;
(b) C=NR$_{11}$, where R$_{11}$ is as previously defined;
(c) C=NC(O)R$_{11}$, where R$_{11}$ is as previously defined;
(d) C=N—OR$_6$, where R$_6$ is selected from:
  1. hydrogen;
  2. —CH$_2$O(CH$_2$)$_2$OCH$_3$,
  3. —CH$_2$O(CH$_2$O)$_n$CH$_3$, where n is as previously defined;
  4. —C$_1$–C$_{12}$ alkyl, optionally substituted with one or more substituents selected from halogen, cyano, aryl, substituted aryl, heteroaryl and substituted heteroaryl;
  5. C$_3$–C$_{12}$ cycloalkyl;
  6. C(O)—C$_1$–C$_{12}$ alkyl);
  7. C(O)—C$_3$–C$_{12}$ cycloalkyl;
  8. C(O)—R$_1$, where R$_1$ is as previously defined; and
  9. —Si(R$_a$)(R$_b$)(R$_c$), wherein R$_a$, R$_b$ and R$_c$ are each independently selected from C$_1$–C$_{12}$ alkyl, aryl and substituted aryl; and
(e) C=N—O—C(R$_7$)(R$_8$)—O—R$_6$, where R$_6$ is as previously defined, provided that R$_6$ is not C(O)—C$_1$–C$_{12}$ alkyl, C(O)—C$_3$–C$_{12}$ cycloalkyl, or C(O)—R$_1$; and R$_7$ and R$_8$ taken together with the carbon atom to which they are attached form a C$_3$–C$_{12}$ cycloalkyl group or each is independently selected from:
  1. hydrogen; and
  2. C$_1$–C$_{12}$ alkyl;

L is selected from:
(a) —CH(OH)CH$_3$;
(b) C$_1$–C$_6$ alkyl, optionally substituted with one or more substituents selected from halogen, cyano, aryl, substituted aryl, heteroaryl and substituted heteroaryl;
(c) C$_2$–C$_6$ alkenyl, optionally substituted with one or more substituents selected from halogen, cyano, aryl, substituted aryl, heteroaryl and substituted heteroaryl; and
(d) C$_2$–C$_6$ alkynyl, optionally substituted with one or more substituents selected from halogen, cyano, aryl, substituted aryl, heteroaryl and substituted heteroaryl;

W is selected from:
(a) hydrogen;
(b) —OH;
(c) —CN;
(d) —OR$_{10}$, where R$_{10}$ is methyl, optionally substituted with one or more substituents selected from:
  1. halogen;
  2. deuterium;
  3. —CN;
  4. —R$_1$, where R$_1$ is as previously defined;
  5. —OR$_{11}$, where R$_{11}$ is as previously defined;
  6. —S(O)$_n$R$_{11}$, where n and R$_{11}$ are as previously defined;
  7. —OC(O)R$_{11}$, where R$_{11}$ is as previously defined;
  8. —C(O)R$_{11}$, where R$_{11}$ is as previously defined;
  9. —C(O)OR$_{11}$, where R$_{11}$ is as previously defined;
  10. —C(O)NHR$_{11}$, where R$_{11}$ is as previously defined;
  11. —OC(O)NHR$_{11}$, where R$_{11}$ is as previously defined;
  12. —NHC(O)R$_{11}$, where R$_{11}$ is as previously defined;

13. —NHC(O)NHR$_{11}$, where R$_{11}$ is as previously defined; and

14. —NHS(O)$_n$R$_{11}$, where n and R$_{11}$ are as previously defined; and (e) —OC(O)NHR$_{11}$, where R$_{11}$ is as previously defined;

Z is selected from:

(a) hydrogen;

(b) —OH;

(c) —OR$_p$, where R$_p$ is as previously defined;

(d) —OR$_{11}$, where R$_{11}$ is as previously defined;

(e) —OC(O)R$_{11}$, where R$_{11}$ is as previously defined;

(f) —OC(O)NHR$_{11}$, where R$_{11}$ is as previously defined;

(g) —S(O)$_n$R$_{11}$, where n and R$_{11}$ are as previously defined;

(h) —

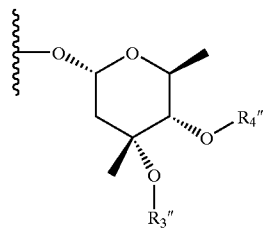

where R$_3$" is hydrogen or methyl; R$_4$" is hydrogen or R$_p$, where R$_p$ is as previously defined; and R$_2$' is hydrogen or R$_p$, where R$_p$ is as previously defined.

In another aspect of the present invention there are disclosed pharmaceutical compositions comprising a therapeutically effective amount of a compound of the invention in combination with a pharmaceutically acceptable carrier, and treatment of antibacterial infections with such compositions. Suitable carriers and methods of formulation are also disclosed. The compounds and compositions of the present invention have antibacterial activity.

In a further aspect of the present invention there are provided processes for the preparation of 11,12-cyclized erythromycin derivatives of formula (I).

DETAILED DESCRIPTION OF THE INVENTION

A first embodiment of the present invention includes compounds represented by formula I, as illustrated above, as well as the pharmaceutically acceptable salts, esters and prodrugs thereof.

A preferred group of compounds of the present invention are those represented by the formula

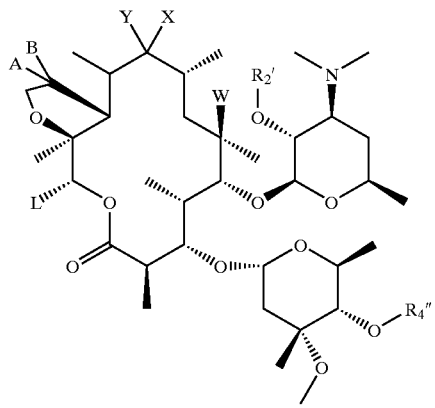

(II)

wherein A, B, L, X, Y, R$_2$' and R$_4$" are as previously defined.

Another preferred group of compounds of the present invention are those represented by formula I wherein L is ethyl and A, B, W, X, Y, Z and R$_2$' are as previously defined.

Representative compounds of the invention are those selected from:

Compound of formula II: A and B taken together with the carbon atom to which they are attached are C=CH$_2$, L is CH$_2$CH$_3$, W is OCH$_3$, X and Y taken together with the carbon atom to which they are attached are C=O, R$_4$" is Bz and R$_2$' is H;

Compound of formula II: A and B taken together with the carbon atom to which they are attached are C=CH$_2$, L is CH$_2$CH$_3$, W is OCH$_3$, X and Y taken together with the carbon atom to which they are attached are C=O, R$_4$" is H and R$_2$' is H;

Compound of formula I: A and B taken together with the carbon atom to which they are attached are C=CH$_2$, L is CH$_2$CH$_3$, W is OCH$_3$, X and Y taken together with the carbon atom to which they are attached are C=O, Z is OH and R$_2$' is H;

Compound of formula II: A and B taken together with the carbon atom to which they are attached are C=CHS(CH$_2$)$_2$-phenyl, L is CH$_2$CH$_3$, W is OCH$_3$, X and Y taken together with the carbon atom to which they are attached are C=O, R$_4$" is Bz and R$_2$' is H;

Compound of formula I: A and B taken together with the carbon atom to which they are attached are C=CHS(CH$_2$)$_2$-phenyl, L is CH$_2$CH$_3$, W is OCH$_3$, X and Y taken together with the carbon atom to which they are attached are C=O, Z is OH and R$_2$' is H;

Compound of formula II: A is H, B is —CH$_2$SC(O)CH$_3$, L is CH$_2$CH$_3$, W is OCH$_3$, X and Y taken together with the carbon atom to which they are attached are C=O, R$_4$" is Bz and R$_2$' is H;

Compound of formula I: A is H, B is —CH$_2$SC(O)CH$_3$, L is CH$_2$CH$_3$, W is OCH$_3$, X and Y taken together with the carbon atom to which they attached are C=O, Z is OH and R$_2$' is H;

Compound of formula I: A is H, B is —CH$_2$SCH$_2$-(4-pyridyl), L is CH$_2$CH$_3$, W is OCH$_3$, X and Y taken together with the carbon atom to which they are attached are C=O, Z is OH and R$_2$' is H;

Compound of formula I: A and B taken together with the carbon atom to which they are attached are C=CHS(CH$_2$)$_2$-phenyl, L is CH$_2$CH$_3$, W is OCH$_3$, X and Y taken together with the carbon atom to which they are attached are C=O, Z is OH and R$_2$' is H;

Compound of formula I: A and B taken together with the carbon atom to which they are attached are C=CHSC(O)CH$_3$, L is CH$_2$CH$_3$, W is OCH$_3$, X and Y taken together with the carbon atom to which they are attached are C=O, Z is OH and R$_2$' is H;

Compound of formula II: A and B taken together with the carbon atom to which they are attached are C=CHSCH$_2$-phenyl, L is CH$_2$CH$_3$, W is OCH$_3$, X and Y taken together with the carbon atom to which they are attached are C=O, R$_4$" is Bz and R$_2$' is H;

Compound of formula II: A and B taken together with the carbon atom to which they are attached are C=O, L is CH$_2$CH$_3$, W is OCH$_3$, X and Y taken together with the carbon atom to which they are attached are C=O, R$_4$" is Bz and R$_2$' is H; or Compound of formula II: A is H and B is OH, L is CH$_2$CH$_3$, W is OCH$_3$, X and Y taken together with the carbon atom to which they are attached are C=O, R$_4$" is H and R$_2$' is H.

Definitions

Listed below are definitions of various terms used to describe this invention. These definitions apply to the terms as they are used throughout this specification and claims, unless otherwise limited in specific instances, either individually or as part of a larger group.

The terms "C$_1$–C$_3$ alkyl," "C$_1$–C6 alkyl," or "C$_1$–C$_{12}$ alkyl," as used herein, refer to saturated, straight- or branched-chain hydrocarbon radicals containing between one and three, one and twelve, or one and six carbon atoms, respectively. Examples of C$_1$–C$_3$ alkyl radicals include methyl, ethyl, propyl and isopropyl radicals; examples of C$_1$–C$_6$ alkyl radicals include, but are not limited to, methyl, ethyl, propyl, isopropyl, n-butyl, tert-butyl, neopentyl and n-hexyl radicals; and examples of C$_1$–C$_{12}$ alkyl radicals include, but are not limited to, ethyl, propyl, isopropyl, n-hexyl, octyl, decyl, dodecyl radicals.

The term "substituted alkyl," as used herein, refers to a "C$_2$–C$_{12}$ alkyl" or "C$_1$–C$_6$ alkyl" group as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$–C$_{12}$-alkyl optionally substituted with halogen, C$_2$–C$_{12}$-alkenyl optionally substituted with halogen, —C$_2$–C$_{12}$-alkynyl optionally substituted with halogen, —NH$_2$, protected amino, —NH—C$_1$–C$_{12}$-alkyl, —NH—C$_2$–C$_{12}$-alkenyl, —NH—C$_2$–C$_{12}$-alkenyl, —NH—C$_3$–C$_{12}$-cycloalkyl, —NH-aryl, —NH-heteroaryl, —NH-heterocycloalkyl, -dialkylamino, -diarylamino, -diheteroarylamino, —O—C$_1$–C$_{12}$-alkyl, —O—C$_2$–C$_{12}$-alkenyl, —O—C$_2$–C$_{12}$-alkenyl, —O—C$_3$–C$_{12}$-cycloalkyl, —O-aryl, —O-heteroaryl, —O-heterocycloalkyl, —C(O)—C$_1$–C$_{12}$-alkyl, —C(O)—C$_2$–C$_{12}$-alkenyl, —C(O)—C$_2$–C$_{12}$-alkenyl, —C(O)—C$_3$–C$_{12}$-cycloalkyl, —C(O)-aryl, —C(O)-heteroaryl, —C(O)-heterocycloalkyl, —CONH$_2$, —CONH—C$_1$–C$_{12}$-alkyl, —CONH—C$_2$–C$_{12}$-alkenyl, —CONH—C$_2$–C$_{12}$-alkenyl, —CONH—C$_3$–C$_{12}$-cycloalkyl, —CONH-aryl, —CONH-heteroaryl, —CONH-heterocycloalkyl, —OCO$_2$—C$_1$–C$_{12}$-alkyl, —OCO$_2$—C$_2$–C$_{12}$-alkenyl, —OCO$_2$—C$_2$–C$_{12}$-alkenyl, —OCO$_2$—C$_3$–C$_{12}$-cycloalkyl, —OCO$_2$-aryl, —OCO$_2$-heteroaryl, —OCO$_2$-heterocycloalkyl, —OCONH$_2$, —OCONH—C$_1$–C$_{12}$-alkyl, —OCONH—C$_2$–C$_{12}$-alkenyl, —OCONH—C$_2$–C$_{12}$-alkenyl, —OCONH—C$_3$–C$_{12}$-cycloalkyl, —OCONH-aryl, —OCONH-heteroaryl, —OCONH-heterocycloalkyl, —NHC(O)—C$_1$–C$_{12}$-alkyl, —NHC(O)—C$_2$–C$_{12}$-alkenyl, —NHC(O)—C$_2$–C$_{12}$-alkenyl, —NHC(O)—C$_3$–C$_{12}$-cycloalkyl, —NHC(O)-aryl, —NHC(O)-heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_2$–C$_{12}$-alkenyl, —NHCO$_2$—C$_3$–C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$–C$_{12}$-alkyl, —NHC(O)NH—C$_2$–C$_{12}$-alkenyl, —NHC(O)NH—C$_2$–C$_{12}$-alkenyl, —NHC(O)NH—C$_3$–C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$–C$_{12}$-alkyl, —NHC(S)NH—C$_2$–C$_{12}$-alkenyl, —NHC(S)NH—C$_2$–C$_{12}$-alkenyl, —NHC(S)NH—C$_3$–C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$–C$_{12}$-alkyl, —NHC(NH)NH—C$_2$–C$_{12}$-alkenyl, —NHC(NH)NH—C$_2$–C$_{12}$-alkenyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, NHC(NH)—C$_1$–C$_{12}$-alkyl, —NHC(NH)—C$_2$–C$_{12}$-alkenyl, —NHC(NH)—C$_2$–C$_{12}$-alkenyl, —NHC(NH)—C$_3$–C$_{12}$-cycloalkyl, —NHC(NH)-aryl, —NHC(NH)-heteroaryl, —NHC(NH)-heterocycloalkyl, —C(NH)NH—C$_1$–C$_{12}$-alkyl, —C(NH)NH—C$_2$–C$_{12}$-alkenyl, —C(NH)NH—C$_2$–C$_{12}$-alkenyl, —C(NH)NH—C$_3$–C$_{12}$-cycloalkyl, —C(NH)NH-aryl, —C(NH)NH-heteroaryl, —C(NH)NH-heterocycloalkyl, —S(O)—C$_1$–C$_{12}$-alkyl, —S(O)—C$_2$–C$_{12}$-alkenyl, —S(O)—C$_2$–C$_{12}$-alkenyl, —S(O)—C$_3$–C$_{12}$-cycloalkyl, —S(O)-aryl, —S(O)-heteroaryl, —S(O)-heterocycloalkyl —SO$_2$NH$_2$, —SO$_2$NH—C$_1$–C$_{12}$-alkyl, —SO$_2$NH—C$_2$–C$_{12}$-alkenyl, —SO$_2$NH—C$_2$–C$_{12}$-alkenyl, —SO$_2$NH—C$_3$–C$_{12}$-cycloalkyl, —SO$_2$NH-aryl, —SO$_2$NH-heteroaryl, —SO$_2$NH-heterocycloalkyl, —NHSO$_2$—C$_1$–C$_{12}$-alkyl, —NHSO$_2$—C$_2$–C$_{12}$-alkenyl, —NHSO$_2$—C$_2$–C$_{12}$-alkenyl, —NHSO$_2$—C$_3$–C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$–C$_{12}$-cycloalkyl, -methoxymethoxy, -methoxyethoxy, —SH, —S—C$_1$–C$_{12}$-alkyl, —S—C$_2$–C$_{12}$-alkenyl, —S—C$_2$–C$_{12}$-alkenyl, —S—C$_3$–C$_{12}$-cycloalkyl, —S-aryl, —S-heteroaryl, —S-heterocycloalkyl, or methylthiomethyl.

The terms "C$_2$–C$_{12}$ alkenyl" or "C$_2$–C$_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, and the like.

The term "substituted alkenyl," as used herein, refers to a "C$_2$–C$_{12}$ alkenyl" or "C$_2$–C$_6$ alkenyl" group as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$–C$_2$-alkyl optionally substituted with halogen, C$_2$–C$_{12}$-alkenyl optionally substituted with halogen, —C$_2$–C$_{12}$-alkynyl optionally substituted with halogen, —NH$_2$, protected amino, —NH—C$_1$–C$_{12}$-alkyl, —NH—C$_2$–C$_{12}$-alkenyl, —NH—C$_2$–C$_{12}$-alkenyl, —NH—C$_3$–C$_{12}$-cycloalkyl, —NH-aryl, —NH-heteroaryl, —NH-heterocycloalkyl, -dialkylamino, -diarylamino, -diheteroarylamino, —O—C$_1$–C$_{12}$-alkyl, —O—C$_2$–C$_{12}$-alkenyl, —O—C$_2$–C$_{12}$-alkenyl, —O—C$_3$–C$_{12}$-cycloalkyl, —O-aryl, —O-heteroaryl, —O-heterocycloalkyl, —C(O)—C$_1$–C$_{12}$-alkyl, —C(O)—C$_2$–C$_{12}$-alkenyl, —C(O)—C$_2$–C$_{12}$-alkenyl, —C(O)—C$_3$–C$_{12}$-cycloalkyl, —C(O)-aryl, —C(O)-heteroaryl, —C(O)-heterocycloalkyl, —CONH$_2$, —CONH—C$_1$–C$_{12}$-alkyl, —CONH—C$_2$–C$_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —$NHC(O)NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, $NHC(S)NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —$NHC(NH)NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl-$SO_2NH_2$, —$SO_2NH$—$C_1$–$C_{12}$-alkyl, —$SO_2NH$—$C_2$–$C_{12}$-alkenyl, —$SO_2NH$—$C_2$–$C_{12}$-alkenyl, —$SO_2NH$—$C_3$–$C_{12}$-cycloalkyl, —$SO_2NH$-aryl, —$SO_2NH$-heteroaryl, —$SO_2NH$-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The terms "$C_2$–$C_{12}$ alkynyl" or "$C_2$–$C_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "$C_2$–$C_{12}$ alkynyl" or "$C_2$–$C_6$ alkynyl" group as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —$NHC(O)NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, $NHC(S)NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —$NHC(NH)NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl-$SO_2NH_2$, —$SO_2NH$—$C_1$–$C_{12}$-alkyl, —$SO_2NH$—$C_2$–$C_{12}$-alkenyl, —$SO_2NH$—$C_2$–$C_{12}$-alkenyl, —$SO_2NH$—$C_3$–$C_{12}$-cycloalkyl, —$SO_2NH$-aryl, —$SO_2NH$-heteroaryl, —$SO_2NH$-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "$C_1$–$C_6$ alkoxy," as used herein, refers to a $C_1$–$C_6$ alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The terms "halo" and "halogen," as used herein, refer to an atom selected from fluorine, chlorine, bromine and iodine.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "substituted aryl," as used herein, refers to an aryl group, as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —$NHC(O)NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, $NHC(S)NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —$NHC(NH)NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl-$SO_2NH_2$, —$SO_2NH$—$C_1$–$C_{12}$-alkyl, —$SO_2NH$—$C_2$–$C_{12}$-alkenyl, —$SO_2NH$—$C_2$–$C_{12}$-alkenyl, —$SO_2NH$—$C_3$–$C_{12}$-cycloalkyl, —$SO_2NH$-aryl, —$SO_2NH$-heteroaryl, —$SO_2NH$-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "arylalkyl," as used herein, refers to a $C_1$–$C_3$ alkyl or $C_1$–$C_6$ alkyl residue attached to an aryl ring. Examples include, but are not limited to, benzyl, phenethyl and the like.

The term "substituted arylalkyl," as used herein, refers to an arylalkyl group, as previously defined, substituted by independent replacement or one, two, or three of the hydrogen atoms thereon with substituents including, but not limited to, but not limited to, —F, —Cl, —Br, —I, —OH, protected hydroxy, —$NO_2$, —CN, —$C_1$–$C_2$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O-$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —$NHC(O)NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, $NHC(S)NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —$NHC(NH)NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC (NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl-$SO_2NH_2$, —$SO_2NH$—$C_1$–$C_{12}$-alkyl, —$SO_2NH$—$C_2$–$C_{12}$-alkenyl, —$SO_2NH$—$C_2$–$C_{12}$-alkenyl, —$SO_2NH$—$C_3$–$C_{12}$-cycloalkyl, —$SO_2NH$-aryl, —$SO_2NH$-heteroaryl, —$SO_2NH$-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_2$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "heteroaryl," as used herein, refers to a mono-, bi-, or tricyclic aromatic radical or ring having from five to ten ring atoms of which one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "substituted heteroaryl," as used herein, refers to a heteroaryl group as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_1$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)heteroaryl, —S(O)-heterocycloalkyl-$SO_2NH_2$, —$SO_2NH$—$C_1$–$C_{12}$-alkyl; —$SO_2NH$—$C_2$–$C_{12}$-alkenyl, —$SO_2NH$—$C_2$–$C_{12}$-alkenyl, —$SO_2NH$—$C_3$–$C_{12}$-cycloalkyl, —$SO_2NH$-aryl, —$SO_2NH$-heteroaryl, —$SO_2NH$-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "$C_3$–$C_{12}$-cycloalkyl," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl.

The term "substituted $C_3$–$C_{12}$-cycloalkyl," as used herein, refers to a $C_3$–$C_{12}$-cycloalkyl group as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O-$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—

$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —$NHC(O)NH_2$, $NHC(O)NH$—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, $NHC(S)NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —$NHC(NH)NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —$S(O)C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl-$SO_2NH_2$, —$SO_2NH$—$C_1$–$C_{12}$-alkyl, —$SO_2NH$—$C_2$–$C_{12}$-alkenyl, —$SO_2NH$—$C_2$–$C_{12}$-alkenyl, —$SO_2NH$—$C_3$–$C_{12}$-cycloalkyl, —$SO_2NH$-aryl, —$SO_2NH$-heteroaryl, —$SO_2NH$-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "heterocycloalkyl," as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heterocycloalkyl," as used herein, refers to a heterocycloalkyl group, as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_2$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —$NHC(O)NH_2$, $NHC(O)NH$—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, $NHC(S)NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —$NHC(NH)NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl-$SO_2NH_2$, —$SO_2NH$—$C_1$–$C_{12}$-alkyl, —$SO_2NH$—$C_2$–$C_{12}$-alkenyl, —$SO_2NH$—$C_2$–$C_{12}$-alkenyl, —$SO_2NH$—$C_3$–$C_{12}$-cycloalkyl, —$SO_2NH$-aryl, —$SO_2NH$-heteroaryl, —$SO_2NH$-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_1$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "heteroarylalkyl," as used herein, refers to a $C_1$–$C_3$ alkyl or $C_1$–$C_6$ alkyl residue residue attached to a heteroaryl ring. Examples include, but are not limited to, pyridinylmethyl, pyrimidinylethyl and the like.

The term "substituted heteroarylalkyl," as used herein, refers to a heteroarylalkyl group, as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl-$SO_2NH_2$, —$SO_2$NH—$C_1$–$C_{12}$-alkyl, —$SO_2$NH—$C_2$–$C_{12}$-alkenyl, —$SO_2$NH—$C_2$–$C_{12}$-alkenyl, —$SO_2$NH—$C_3$–$C_{12}$-cycloalkyl, —$SO_2$NH-aryl, —$SO_2$NH-heteroaryl, —$SO_2$NH-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "$C_1$–$C_6$ alkoxy," as used herein, refers to a $C_1$–$C_6$ alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The term "$C_1$–$C_3$-alkyl-amino," as used herein, refers to one or two $C_1$–$C_3$-alkyl groups, as previously defined, attached to the parent molecular moiety through a nitrogen atom. Examples of $C_1$–$C_3$-alkyl-amino include, but are not limited to, methylamino, dimethylamino, ethylamino, diethylamino, and propylamino.

The term "alkylamino" refers to a group having the structure —NH($C_1$–$C_{12}$ alkyl) where $C_1$–$C_{12}$ alkyl is as previously defined.

The term "dialkylamino" refers to a group having the structure —N($C_1$–$C_{12}$ alkyl) ($C_1$–$C_{12}$ alkyl), where $C_1$–$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$–$C_{12}$ alkyl) or —C(O)N($C_1$–$C_{12}$ alkyl)($C_1$–$C_{12}$ alkyl), —C(O)$NH_2$, and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis*, 3rd edition, John Wiley & Sons, New York (1999). Examples of hydroxy protecting groups include, but are not limited to, methylthiomethyl, tert-butyldimethylsilyl, tert-butyidiphenylsilyl, acyl substituted with an aromatic group and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis*, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

"An effective amount," as used herein, refers to an amount of a compound which confers a therapeutic effect on the treated subject. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1–19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus*, or Peptostreptococcus spp. Pseudomonas spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *S. pyogenes, S. agalactiae*, Streptococcal groups C–F (minute-colony streptococci), viridans streptococci, Corynebacterium spp., Clostridium spp., or *Bartonella henselae*; uncomplicated acute urinary tract infections related to infection by *S. saprophyticus* or Enterococcus spp.; urethritis and cervicitis; and sexually transmitted diseases related to infection by *Chlamydia trachomatis, Haemophilus ducreyi, Treponema pallidum, Ureaplasma urealyticum*, or *Nesseria gonorrheae*; toxin diseases related to infection by *S. aureus* (food poisoning and Toxic shock syndrome), or Groups A, S, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae*, or Listeria spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by Cryptosporidium spp. odontogenic infection related to infection by viridans streptococci; persistent cough related to infection by *Bordetella pertussis*; gas gangrene related to infection by *Clostridium perfringens* or Bacteroides spp.; Skin infection by *S. aureus*, Propionibacterium acne; atherosclerosis related to infection by *Helicobacter pylori* or *Chlamydia pneumoniae*; or the like.

Bacterial infections and protozoa infections and disorders related to such infections that may be treated or prevented in animals include, but are not limited to, the following: bovine respiratory disease related to infection by *P. haemolytica, P. multocida, Mycoplasma bovis*, or Bordetella spp.; cow enteric disease related to infection by *E. coli* or protozoa (i.e., coccidia, cryptosporidia, etc.), dairy cow mastilis related to infection by *S. aureus, S. uberis, S. agalactiae, S. dysgalactiae*, Klebsiella spp., Corynebacterium, or Enterococcus spp.; swine respiratory disease related to infection by *A. pleuropneumoniae, P. multocida*, or Mycoplasma spp.; swine enteric disease related to infection by *E. coli, Lawsonia intracellularis*, Salmonella spp., or *Serpulina hyodyisinteriae*; cow footrot related to infection by Fusobacterium spp.; cow metritis related to infection by *E. coli*; cow hairy warts related to Infection by *Fusobacterium necrophorum* or *Bacteroides nodosus*; cow pink-eye related to infection by *Moraxella bovis*, cow premature abortion related to infection by protozoa (i.e. neosporium); urinary tract infection in dogs and cats related to infection by *E. coli*; skin and soft tissue infections in dogs and cats related to infection by *S. epidermidis, S. intermedius*, coagulase neg. Staphylococcus or *P. multocida*; and dental or mouth infections in dogs and cats related to infection by Alcaligenes spp., Bacteroides spp., Clostridium spp., Enterobacter spp., Eubacterium spp., Peptostreptococcus spp., Porphfyromonas spp., Campylobacter spp., Actinomyces spp., Erysipelothrix spp., Rhodococcus spp., Trypanosoma spp., Plas,odium spp., Babesia spp., Toxoplasma spp., Pneumocystis spp., Leishmania spp., and Trichomonas spp. or Prevotella spp. Other bacterial infections and protozoa infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiler plates utilizing the appropriate Mueller Hinton Broth medium (CAMHB) for the observed bacterial isolates. Antimicrobial agents were serially diluted (2-fold) in DMSO to produce a concentration range from about 64 µg/ml to about 0.03 µg/ml. The diluted compounds (2 µl/well) were then transferred into sterile, uninoculated CAMHB (0.2 mL) by use of a 96 fixed tip-pipetting station. The inoculum for each bacterial strain was standardized to $5 \times 10^5$ CFU/mL by optical comparison to a 0.5 McFarland turbidity standard. The plates were inoculated with 10 µl/well of adjusted bacterial inoculum. The 96 well plates were covered and incubated at 35+/−2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 µg/ml to about 0.03 µg/ml.

All in vitro testing follows the guidelines described in the Approved Standards M7-A4 protocol, published by the National Committee for Clinical Laboratory Standards (NCCLS).

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filler, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or other animals by administering to the patient a therapeutically effective amount of a compound of the invention, in such amounts and for such time as is necessary to achieve the desired result.

By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention 4 will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required, Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath.

The dosage for the treatment of fish differs depending upon the purpose of administration (prevention or cure of disease) and type of administration, size and extent of infection of the fish to be treated. Generally, a dosage of 5–1000 mg, preferably 20–100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which may be used in the descriptions of the schemes and the examples that follow are: Ac for acetyl; AIBN for 2,2-azobisisobutyronitrile; Bn for benzyl; Boc for t-butoxycarbonyl; Bu$_3$SnH for tributyltin hydride; Bz for benzoyl; CDI for carbonyidiimidazole; dba for dibenzylidene acetone; dppb for diphenylphosphino butane; DBU for 1,8-diazabicyclo[5.4.0]undec-7-ene; DCC for 1,3-dicyclohexylcarbodiimide; DEAD for diethylazodicarboxylate; DIBAL-H for diisopropyl aluminum hydride; DIC for 1,3-diisopropylcarbodiimide; DIEA for diisopropylethylamine; DMAP for dimethylaminopyridine; DMF for dimethyl formamide; DMSO for dimethylsulfoxide; DPPA for diphenylphosphoryl azide; LAH for lithium aluminum hydride; EtOAc for ethyl acetate; KHMDS for potassium bis(trimethylsilyl)amide; LDA for lithium diisopropyl amide; MeOH for methanol; Me$_2$S for dimethyl sulfide; MOM for methoxymethyl; OMs for mesylate; OTos for tosylate; NaN(TMS)$_2$ for sodium bis(trimethylsilyl)amide; NCS for N-chlorosuccinimide; NMMO for 4-methylmorpholine N-oxide; PCC for pyridinium chlorochromate; PDC for pyridinium dichromate; Ph for phenyl; POPd for dihydrogen dichlorobis(di-tert-butylphosphino) palladadium(II); TEA for triethylamine; THF for tetrahydrofuran; TPP or PPh$_3$ for triphenylphosphine; TBS for tert-butyl dimethylsilyl; and TMS for trimethylsilyl.

Synthetic Methods

The compounds and processes of the present invention will be better understood in connection with the following synthetic schemes which are illustrative of the methods by which the compounds of the invention may be prepared. The groups A, B, W, X, Y, Z, R$_2$, R$_2$', R$_4$" and R$_{11}$ are as previously defined unless otherwise noted below.

A preferred intermediate for the preparation of compounds represented by formula I is a compound represented by formula III as illustrated below:

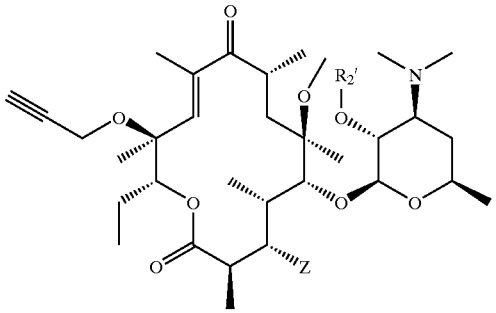

(III)

where R$_2$' and Z are as previously defined

Another preferred intermediate for the preparation of compounds represented by formula I is a compound represented by the formula IV as illustrated below:

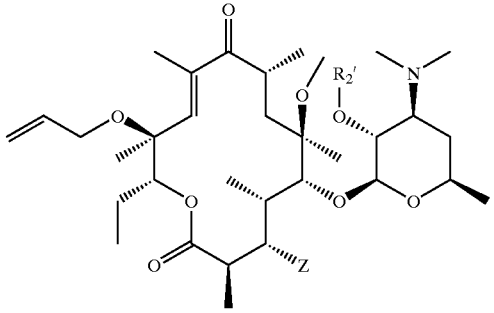

(IV)

where R$_2$' and Z are as previously defined.

Scheme 1

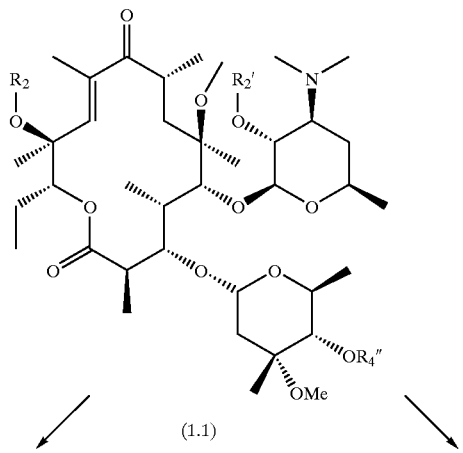

(1.1)

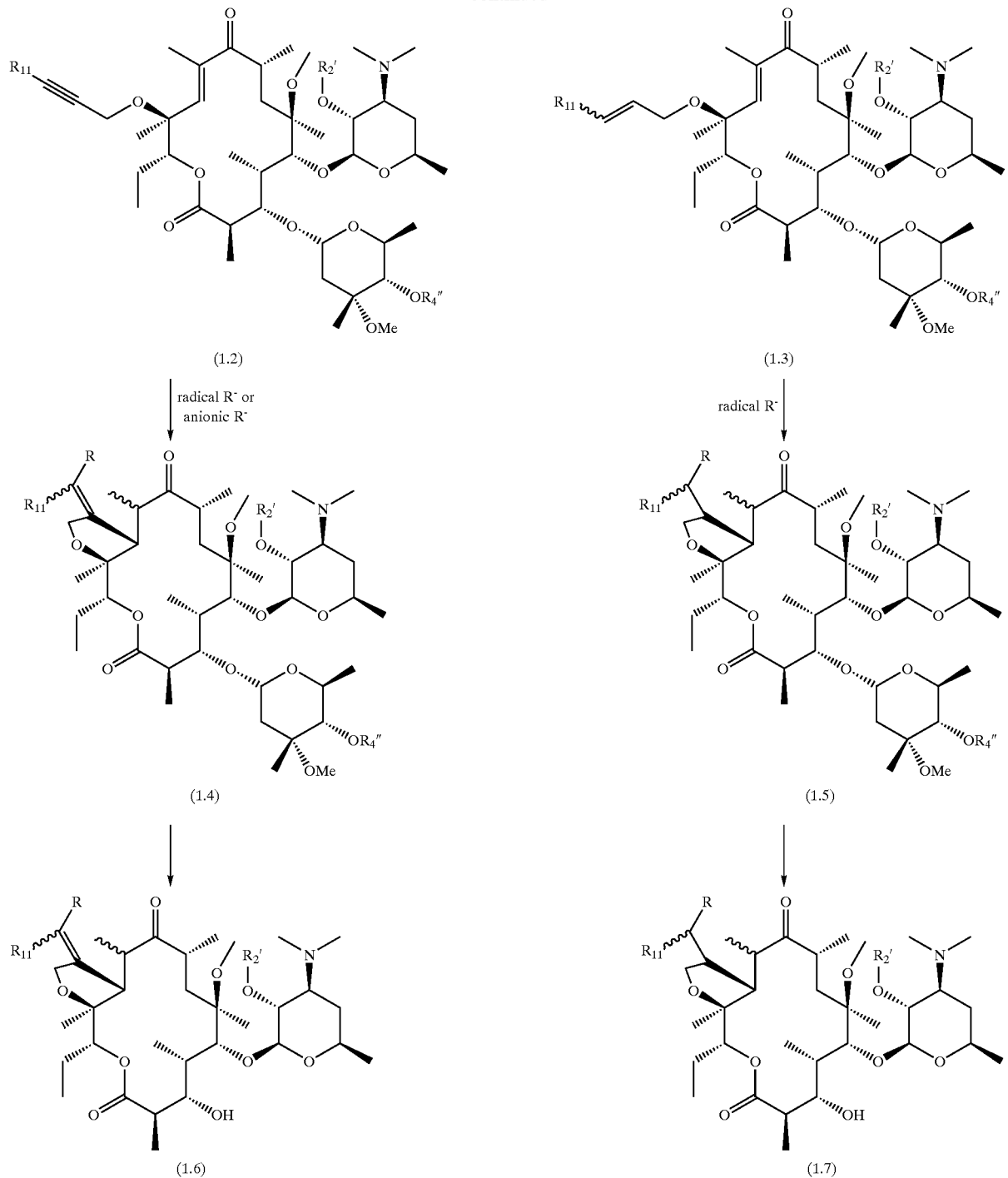

(1.2) (1.3) (1.4) (1.5) (1.6) (1.7)

A process of the invention for the preparation of compounds of formula I, as illustrated in Scheme 1, involves preparing compounds of formula (1.4) and (1.5) by a tandem radical or anionic addition and cyclization of compounds of formula (1.2) or (1.3).

Intermediates (1.2) and (1.3) can be prepared by alkylation of the readily available compounds of formula (1.1), where $R_2$ is hydrogen, which can be prepared according to the process described by Baker et al. *J. Org. Chem.* 1988, 53, 2340–2345; Elliott et al. *J. Med. Chem.* 1988, 41, 1651–1659; Ma et al. *J. Med. Chem.* 2001, 44, 41374156, and Or et al. U.S. Pat. No. 6,075,011-B1. Typical alkylating conditions include treating compounds of formula (1.1) with a suitable alkylating agent, such as propargyl halide, allyl halide, allyl mesylate or the like, in the presence of a base such as $K_2CO_3$, NaOH, NaH, LDA or the like, optionally with a phase transfer catalyst such as tetrabutylammonium iodide, 18-crown-6 or the like, in THF, toluene, methylene chloride, DMF, DMSO, water or the like, or combinations thereof, at from about −50° C. to about 100° C. for 1 hour to 24 hours to provide compounds of formula (1.2) and (1.3). Alternatively, compounds of formula (1.3) can be obtained by reaction of a suitable alkylating agent such as tert-butyl allyl carbonate, tert-butyl 2-butenyl carbonate, allyl acetate, allyl benzoate or the like, in the presence of a palladium catalyst, such as palladium(II) acetate, tetrakis (triphenylphosphine)palladium(0), tris (dibenzylideneacetone)dipalladium(0), tetra (dibenzylideneacetone)dipalladium(0), palladium on carbon or the like, and a suitable phosphine ligand, such as triphenylphosphine, bis(diphenylphosphino)methane, 1,2-bis(diphenylphosphino)ethane, 1,3-bis(diphenylphosphino) propane, 1,4-bis(diphenylphosphino)butane, tri-o-tolyl-phosphine, or the like, in an aprotic solvent, such as tetrahydrofuran, N,N-dimethylformamide, dimethyl sulfoxide, N-methyl-2-pyrrolidinone, hexamethylphosphoric triamide, 1,2-dimethoxyethane, methyl-tert-butyl ether, heptane, acetonitrile, acetonitrile and ethyl acetate or the like, at from 40° C. to about 150° C. for 0.5 hour to about 48 hours.

In accordance with Scheme 1, compounds of formula I (1.4) and (1.5) of the present invention can be prepared by methods which are well known in the art involving a tandem radical addition and cyclization of intermediates (1.2) and (1.3) with a suitable radical species (R') which can be generated from a radical precursor and an initiator. The radical R' can be centered as, but not limited to, carbon, silicon, tin, oxygen, sulfur, nitrogen, halogen with non-, mono-, di- or tri-substitution depending on the nature of the radical centered atom. A typical radical of this process is selected from, but not limited to, a group consisting of $PhCH_2'$, $Et_3Si'$, $(n-Bu)_3Sn'$, $tert-BuO'$, $AcS'$, $PhCH_2CH_2S'$ and Br'. A typical radical precursor for this process is selected from, but not limited to, $C_1-C_{12}$ alkyl halide, $C_2-C_6$ alkenyl halide, $C_2-C_6$ alkynyl halide, $C_2-C_6$ alkenyl tri $(C_1-C_{12}$ alkyl)stannane, tri($C_1-C_{12}$ alkyl)stannane, hexamethyldistannane, trichlorosilane, triphenylsilane, tert-butyl hydrogen peroxide, thiolacetic acid, phenyl disulfide, N-bromosuccinamide and bromine. A typical radical initiator of this process can be selected from, but not limited to, a group consisting of AIBN, tert-butyl peroxide, benzoyl peroxide. The preferred radical reaction conditions of the present invention includes reacting the compounds of formula (1.2) or (1.3) with a radical generated from a group consisting of, but not limited to, halide, stannane, distannane, silane, mercaptan or disulfide, in the presence of AIBN, optionally in the presence of a reducing agent such as tributylstannane, diphenylsilane, sodium borohydride, magnesium, lithium aluminum hydride or the like, at 40° C. to 150° C. for a period of from 1 hour to 10 days, in an aprotic solvents, such as tetrahydrofuran, N,N-dimethylformamide, dimethyl sulfoxide, N-methyl-2-pyrrolidinone, 1,2-dimethoxyethane, methyl-tert-butyl ether, cyclohexane, heptane, acetonitrile, benzene, toluene and ethyl acetate or the like.

Alternatively compounds of formula I (1.4) of the present invention may be prepared by a tandem anionic addition and cyclization of intermediates (1.2) with a suitable anionic species (R⁻) which can be generated from an organometallic precursor. Typically a compound of formula (1.2) is reacted with an organometallic reagents, such as allylmagnesium chloride, methylmagnesium iodide, phenyllithium, triethylaluminum, triethoxysilane, or the like, in the presence of 0–100% molar percent (relative to compound 1.2) of a transitional metal or its salt or its complex such as palladium, iridium, chromium(III) chloride, cerium(III) chloride, palladium(II) acetate, platinum(II) chloride, chloroplatinic acid, nonacabonyliron(0), titanocene (IV) dichloride, bis(1,5-cyclooctadiene)nickel(0), tetrakis (triphenylphosphine)palladium(0) or the like, at −78° C. to 100° C. for a period of from 0.5 to 48 hours, in an aprotic solvents, such as tetrahydrofuran, dimethyl sulfoxide, N-methyl-2-pyrrolidinone, 1,2-dimethoxyethane, methyl-tert-butyl ether, cyclohexane, heptane, acetonitrile, benzene and toluene or the like.

Another process of the invention involves the removal of the cladinose moiety of the compounds of formula I. The cladinose moiety of the macrolide compounds of formulae (1.4) and (1.5) can be removed to give compounds of formulae (1.6) and (1.7) in Scheme 1 by a dilute acid, such as hydrochloric acid, sulfuric acid, perchloric acid, nitric acid, chloroacetic acid, dichloroacetic acid, trifluoroacetic acid and p-toluenesulfonic acid or the like, in a suitable solvent, such as methanol, ethanol, isopropanol, butanol, water or the like, or the mixtures thereof, at 0° C. to about 80° C. for 0.5 hour to 24 hours.

When $R_2''$ is an acyl protecting group, it can be removed upon treatment with methanol at from room temperature to 60° C. When $R_2''$ is a silyl protecting group, the deprotection can be also effected by an acid, such as dilute hydrochloric acid, sulfuric acid, perchloric acid, nitric acid, chloroacetic acid, dichloroacetic acid, trifluoroacetic acid and p-toluenesulfonic acid or the like, or a fluoride, such as tetrabutylammonium fluoride, pyridinium fluoride, ammonium fluoride, hydrofluoric acid or the like, at from 0° C. to 50° C. for 0.5 to 24 hours.

Scheme 2

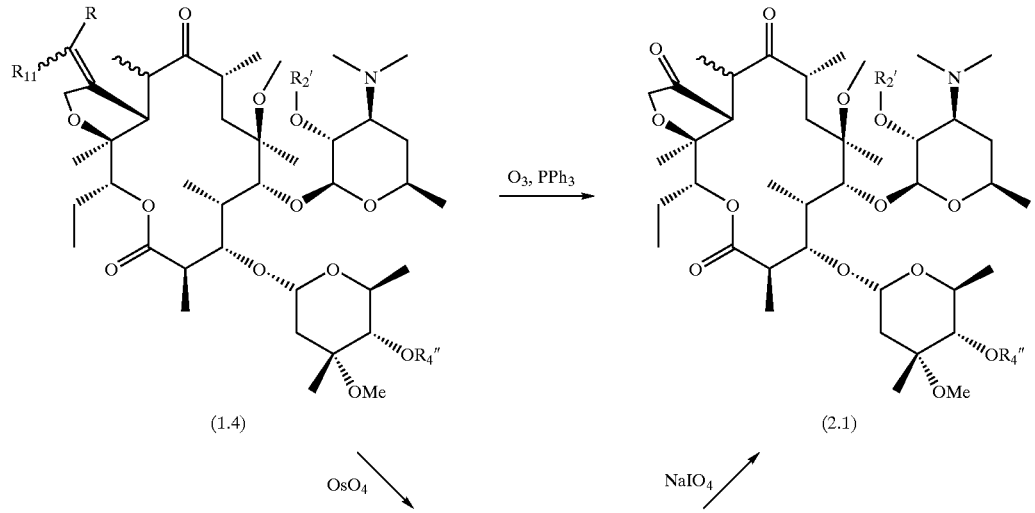

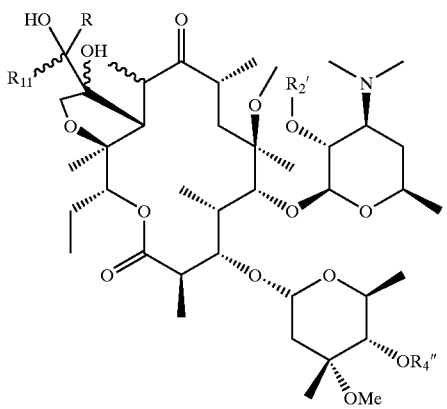

(2.2)

Conversion of the alkene of formula (1.4) into the ketone (2.1) can be accomplished by exposure of the alkene to ozone followed by decomposition of the ozonide intermediate with an appropriate reducing agent, as outlined in Scheme 2. The reaction is typically carried out in a solvent such as, for example, methanol, ethanol, ethyl acetate, glacial acetic acid, chloroform, methylene chloride or hexanes, or mixtures thereof, at from −78° C. to −20° C. Representative reducing agents include, for example, triphenylphosphine, trimethyl phosphite, thiourea, and dimethyl sulfide or the like. A more thorough discussion of ozonolysis and the conditions therefor can be found in M. B. Smith and J. March "Advanced Organic Chemistry" $5^{th}$ ed., Wiley & Son, Inc. 2001.

An alternative method for the preparation of the ketones (2.1) involves dihydroxylation of the alkene followed by diol cleavage. The glycol (2.2) is prepared by reacting the alkene (1.4), either with stoichiometric amounts of osmium tetraoxide, or with catalytic amounts of osmium tetraoxide if an oxidant such as hydrogen peroxide, tert-butyl hydroperoxide, or N-methylmorpholine-N-oxide is present, in a variety of solvents such as 1,4-dioxane, tetrahydrofuran, tert-butanol, acetone, diethyl ether, water or the like, or the mixture thereof, preferably at from 0° C. to 50° C.

The glycol (2.2) can be cleaved by a variety of reagents including, but not limited to, periodic acid, lead tetraacetate, manganese dioxide, potassium permanganate, sodium metaperiodate, and N-iodosuccinamide in a variety of solvents such as 1,4-dioxane, tetrahydrofuran, tert-butanol, acetone, ethanol, methanol, water or the like, or the mixture thereof, at from 0° C. to 50° C.

The synthesis of the ketone (2.1) can also be realized in one-pot by reacting the alkene (1.4) with either stoichiometric amounts or catalytic amounts of osmium tetraoxide and a glycol cleavage reagent, such as, for example, periodic acid, lead tetraacetate, manganese dioxide, potassium permanganate, sodium metaperiodate, and N-iodosuccinamide or the like, in a solvent such as 1,4-dioxane, tetrahydrofuran, tert-butanol, acetone, ethanol, methanol, water or the like, or mixtures thereof, at from 0° C. to 50° C.

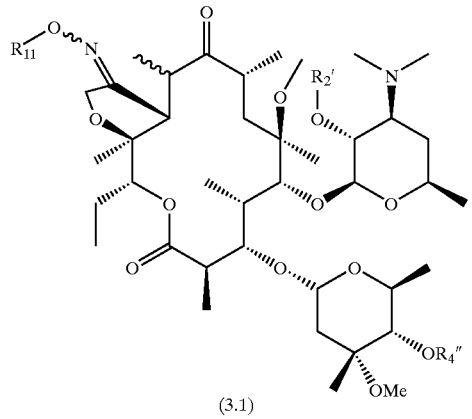

(3.1)

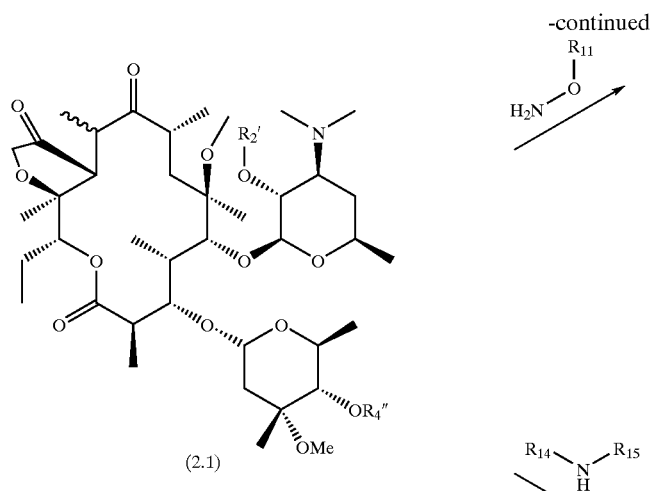

(2.1)

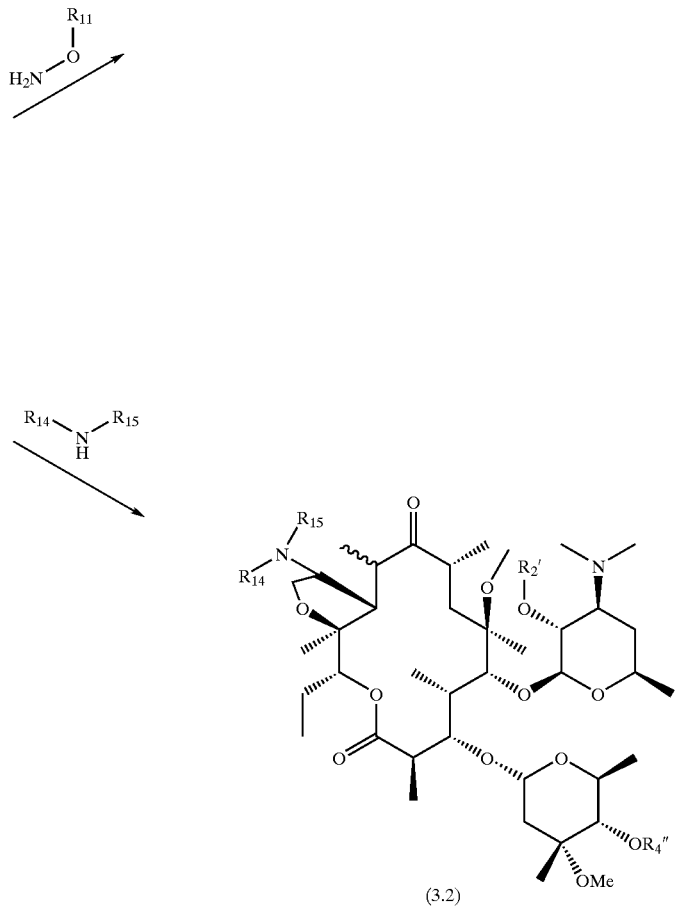

(3.2)

Compounds of formula (2.1) represent useful intermediates which can be further functionalized in a variety of ways. Scheme 3 details procedures for the conversion of the ketone (2.1) into an oxime of formula (3.1) or an amine of formula (3.2). The formation of oxime (3.1) can be accomplished under either acidic or basic conditions in a variety of solvents such as, for example, methanol, ethanol, water, tetrahydrofuran, 1,2-dimethoxyethane, ethyl acetate, or mixtures thereof, at from 0° C. to 70° C. over a period of 10 minutes to 12 hours. Representative acids include, but are not limited to, hydrochloric acid, phosphoric acid, sulfuric acid, p-toluenesulfonic acid, acetic acid and pyridinium p-toluenesulfonate. Bases which are useful are, for example, triethylamine, pyridine, diisopropylethyl amine, 2,6-lutidine, imidazole and potassium carbonate, and the like. The formation of amines (3.2) can be accomplished by reacting a ketone (2.1) with a primary or secondary amine and a suitable reducing agent such as, for example, hydrogen, sodium borohydride, sodium cyanoborohydride, LAH, zinc, DIBAL-H, triethylsilane, ammonium formate and the like, optionally in the presence of a catalyst such as Raney Ni, palladium on carbon, platinum dioxide, tetrakis (triphenylphosphine)palladium and the like in a suitable solvent such as methanol, acetonitrile, water, tetrahydrofuran, 1,2-dimethoxyethane, ethyl acetate, acetic acid, trifluoroacetic acid, hydrochloric acid or the like, or the mixture thereof, at a pH between 3 and 5 over a period of 5 minutes to 24 hours.

Scheme 4

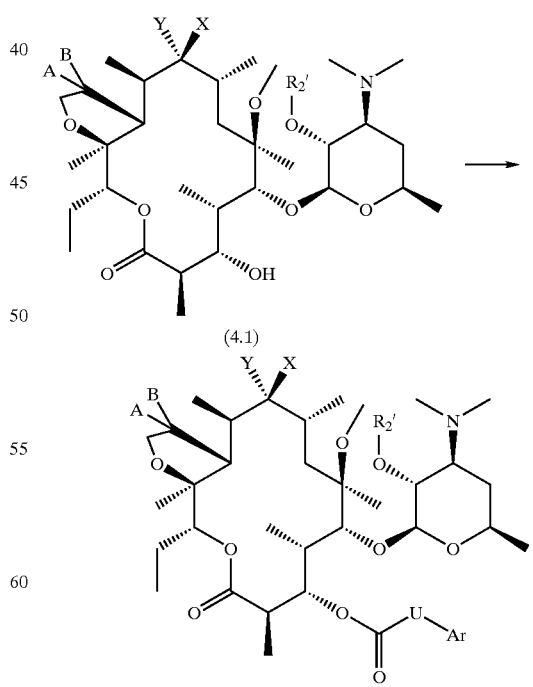

U = O, S, NH or -(CH$_2$)$_n$-
n = 0–4

Scheme 4 illustrates a procedure for the acylation of the C-3 hydroxyl of compounds of formula (4.1). The hydroxyl group is reacted with an acylating agent such as but is not limited to, acid chlorides, acid anhydrides, and chloroformates in the presence of a base such as pyridine, triethylamine, diisopropylethylamine, N-methyl morpholine, N-methyl pyrrolidine, 2,6-lutidine, 1,8-diazabicyclo[5.4.0]undec-7-ene, and DMAP or the like, in an aprotic solvent. For a more extensive discourse on acylating conditions see for example, T. W. Greene and P. G. M. Wuts in "Protective Groups in Organic Synthesis" 3$^{rd}$ ed., John Wiley & Son, Inc, 1999, referred to above herein.

Scheme 5

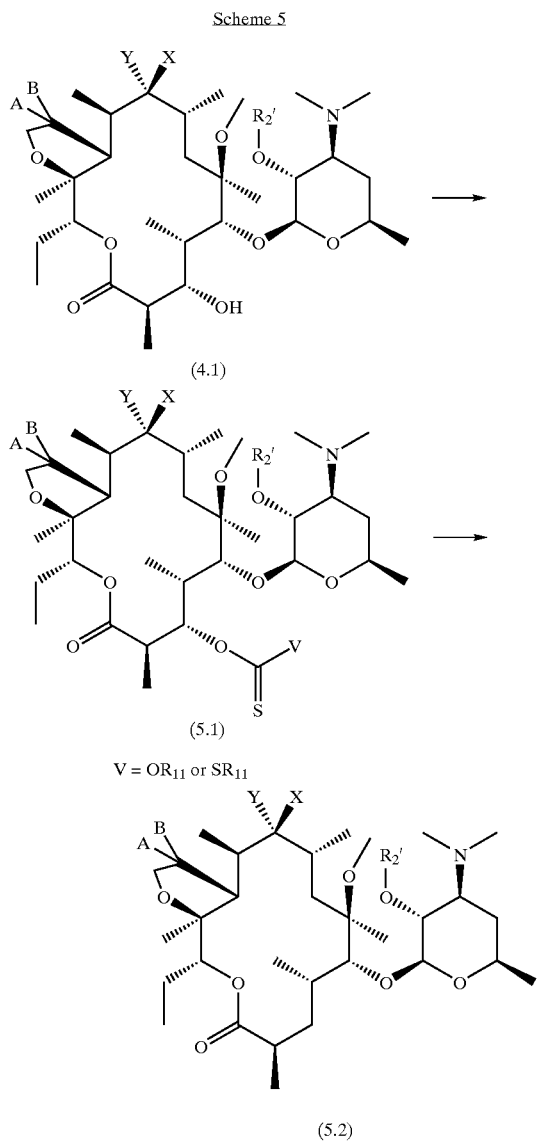

(4.1)

(5.1)

V = OR$_{11}$ or SR$_{11}$ (5.2)

Another process of the invention, as illustrated in Scheme 5, involves the C-3 deoxygenation of the macrolide (4.1) which can be accomplished via a two step procedure shown therein through a xanthate or thiocarbonate of formula (5.1). In the first step, the xanthate is formed by the reaction of alkoxide of alcohol (4.1) with an appropriate thiocarbonyl reagent, such as carbondisulfide followed by methyliodide, or a dithiocarbonyl imidazole; whereas the thiocarbonate can be prepared by the reaction of the alkoxide with either thiocarbonyldiimidazole followed by methanol, ethanol or the like, or a thiochloroformate. One skilled in the art will appreciate that other reagents and conditions exist to perform these transformations and that the examples above are for illustrative purposes only and do not limit the scope of this invention. These reactions are typically run in a polar aprotic solvent, such as tetrahydrofuran, acetonitrile, N,N-dimethylformamide or the like.

In the second step of Scheme 5, the thiocarbonate or xanthate is reduced to give the alkane of formula (5.2). Most typically this is done under radical conditions using, for example, a silane or stannane such as (TMS)$_3$SiH, Ph$_2$SiH$_2$, Bu$_3$SnH, Ph$_3$SnH or the like, and a radical initiator such as AIBN, tert-butyl hydrogen peroxide or the like in an aprotic solvent, such as tetrahydrofuran, N,N-dimethylformamide, dimethyl sulfoxide, N-methyl-2-pyrrolidinone, 1,2-dimethoxyethane, methyl tert-butyl ether, cyclohexane, heptane, acetonitrile, benzene, toluene and ethyl acetate or the like, at 0° C. to 150° C. for a period of from 1 hour to 10 days.

EXAMPLES

The compounds and processes of the present invention will be described further in detail with respect to specific preferred embodiments by way of examples, it being understood that these are intended to be illustrative only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of formula II: A and B taken together with the carbon atom to which they are attached are C=CH$_2$, L is CH$_2$CH$_3$, W is OCH$_3$, X and Y taken together with the carbon atom to which they are attached are C=O, R$_4$" is Bz and R$_2$' is H.

Step 1a. Compound of formula 1.1 of Scheme 1: R$_2$ is H, R$_2$' is Bz and R$_4$" is Bz.

A solution of compound 1.1 of Scheme 1, wherein R$_2$, R$_2$' and R$_4$" are H (prepared according to Elliott et al. *J. Med. Chem.* 1998, 41, 1651–1659)(95.91 g, 131.51 mmol) in methylene chloride (1L) containing benzoyl anhydride (90%, 66.26 g, 289.30 mmol), triethylamine (54.81 mL, 433.95 mmol) and DMAP (320 mg, 2.63 mol) was heated to reflux overnight. The resulting mixture was washed with saturated NaHCO$_3$ solution and brine, concentrated under reduced pressure and recrystalized in acetonitrile to give 77.30 g of the title compound as a white solid.

MS (ESI) m/z=938 (M+H)$^+$.

$^{13}$C-NMR (125 MHz, CDCl$_3$): δ 207.6, 175.2, 166.2, 165.2, 141.2, 138.9, 133.4, 132.5, 130.8, 129.7, 128.4, 128.1, 100.6, 95.9, 80.0, 79.6, 78.9, 78.3, 78.0, 73.2, 72.9, 72.4, 67.7, 63.7, 63.4, 50.6, 49.7, 44.9, 40.9, 39.7, 38.5, 35.4, 31.8, 22.2, 21.7, 21.3, 21.2, 18.7, 18.3, 15.5, 13.7, 10.6, 9.8.

Step 1b. Compound of formula 1.2 of Scheme 1: R$_{11}$ is H, R$_2$' is Bz and R$_4$" is Bz.

A mixture of the compound from Step 1a (3.40 g, 3.62 mmol), tetrabutylammonium iodide (268 mg, 0.72 mmol), methylene chloride (15.0 mL), propargyl bromide (80% in toluene, 2.42 mL, 21.7 mmol) and sodium hydroxide (50% in water, 15.0 mL) was stirred at room temperature for 3 hours. The mixture was partitioned (ethyl acetate and water). The organic phases were washed with water and brine, dried (Na$_2$SO$_4$) and evaporated. The residue was purified by chromatography (silica, hexanes:acetone/95:5 and 9:1) to give 1.32 g (37%) of the title compound.

MS ESI) m/z=976 (M+H)$^+$.

$^{13}$C-NMR (125 MHz, CDCl$_3$): δ 205.7, 174.7, 166.1, 165.2, 140.9, 137.2, 133.3, 132.5, 130.8, 129.8, 129.6, 128.4, 128.1, 100.6, 96.1, 80.2, 79.9, 78.9, 78.8, 78.3, 78.1, 76.3, 73.8, 72.8, 72.3, 67.7, 63.7, 63.3, 51.2, 50.7, 49.7, 45.2, 40.8, 39.7, 39.1, 38.4, 35.5, 31.7, 22.2, 21.8, 21.2, 21.1, 19.7, 18.4, 18.3, 16.3, 13.0, 10.2, 9.8.

Step 1c. Compound 1.4 of Scheme 1: R is SnBu$_3$, R$_{11}$ is H, R$_2$' is Bz and R$_4$" is Bz.

A solution of the compound from Step 1b (57.6 mg, 0.059 mmol) in anhydrous benzene (5.0 mL) was heated to reflux with tributyltin hydride (82 mg, 0.28 mmol) in the presence of AIBN (2 mg) for 2.5 hours before chromatography (silica, hexanes:acetone/95:5) to give the title compound (46.0 mg, 62%).

MS (ESI) m/z=1266/1268 (M+H)$^+$.

Step 1d. Compound 1.4 of Scheme 1: R is H, R$_{11}$ is H, R$_2$' is Bz and R$_4$" is Bz.

A solution of the compound from Step 1c (46.0 mg, 0.036 mmol) in ethanol (2.0 mL) was treated with hydrochloric acid (2 M, 2.0 mL) at room temperature for 15 minutes. The mixture is partitioned (ethyl acetate and saturated NaHCO$_3$). The organic phase is washed with water and brine, dried (Na$_2$SO$_4$) and evaporated. The residue is purified by chromatography to give the title compound.

MS (ESI) m/z=978 (M+H)$^+$.

Step 1e. Compound of formula II: A and B taken together with the carbon atom to which they are attached are C=CH$_2$, L is CH$_2$CH$_3$, W is OCH$_3$, X and Y taken together with the carbon atom to which they are attached are C=O, R$_4$" is Bz and R$_2$' is H.

A solution of the compound from Step 1d in methanol is refluxed for 24 hours, evaporated and purified by column chromatography to give the title compound.

Example 2

Compound of formula II: A and B taken together with the carbon atom to which they are attached are C=CH$_2$, L is CH$_2$CH$_3$, W is OCH$_3$, X and Y taken together with the carbon atom to which they are attached are C=O, R$_4$" is H and R$_2$' is H.

The compound of Example 1 is treated with lithium hydroxide in THF at reflux temperature, evaporated and purified by column chromatography to give the title compound.

Example 3

Compound of formula II: A and B taken together with the carbon atom to which they are attached are C=CH$_2$, L is CH$_2$CH$_3$, W is OCH$_3$, X and Y taken together with the carbon atom to which they are attached are C=O, Z is OH and R$_2$' is H.

Step 3a. Compound 1.6 of Scheme 1: R is H, R$_{11}$ is H and R$_2$' is Bz.

A solution of the compound from Step 1c (46.0 mg, 0.036 mmol) in ethanol (2.0 mL) was treated with hydrochloric acid (2 M, 2.0 mL) at 50° C. for 3 hours and 60° C. for 2 hours before partition (ethyl acetate and saturated NaHCO$_3$). The organic phases were washed with water and brine, dried (Na$_2$SO$_4$) and evaporated. The residue was purified by chromatography (silica, hexanes:acetone/95:5~4:1) to give the title compound (15.1 mg, 58%).

MS (ESI) m/z=716 (M+H)$^+$.

$^{13}$C-NMR (125 MHz, CDCl$_3$): δ 215.7, 174.8, 165.4, 146.2, 132.8, 130.6, 129.9, 129.7, 128.3, 111.3, 99.9, 86.0, 80.7, 78.4, 77.9, 77.0, 72.0, 70.4, 68.9, 63.4, 49.5, 48.6, 45.7, 44.0, 40.8, 37.4, 35.8, 35.6, 32.1, 21.6, 21.1, 19.4, 19.1, 15.13, 15.07, 14.9, 10.3, 7.7.

Step 3b. Compound of formula I: A and B taken together with the carbon atom to which they are attached are C=CH$_2$, L is CH$_2$CH$_3$, W is OCH$_3$, X and Y taken together with the carbon atom to which they are attached are C=O, Z is OH and R$_2$' is H.

A solution of the compound from Step 3a in methanol is refluxed for 24 hours, evaporated and purified by column chromatography to give the title compound.

Example 4

Compound of formula II: A and B taken together with the carbon atom to which they are attached are C=CHS(CH$_2$)$_2$-phenyl, L is CH$_2$CH$_3$, W is OCH$_3$, X and Y taken together with the carbon atom to which they are attached are C=O, R$_4$" is Bz and R$_2$' is H.

Step 4a. Compound 1.4 of Scheme 1: R is —S(CH$_2$)$_2$-phenyl, R$_{11}$ is H, R$_2$' is H and R$_4$" is Bz.

A solution of the compound from Step 1b (303 mg, 0.31 mmol) in anhydrous benzene (6.2 mL) was heated to reflux with 2-phenylethylthiol (0.10 mL, 0.75 mmol) in the presence of AIBN (8.9 mg) for 21 hours before additional AIBN (3×8.9 mg) was added at every 7~22 hour intervals during a total of 65 hours reaction time. The solution was evaporated and the residue was chromatographed (silica, hexanes:acetone/98:2~9:1) to give the title compound (200 mg, 58%).

MS (ESI) m/z=1114 (M+H)$^+$.

Step 4b. Compound of formula I: A and B taken together with the carbon atom to which they are attached are C=CHS(CH$_2$)$_2$-phenyl, L is CH$_2$CH$_3$, W is OCH$_3$, X and Y taken together with the carbon atom to which they are attached are C=O, R$_4$" is Bz and R$_2$' is H.

A solution of the compound from Step 4a in methanol is refluxed for 24 hours, evaporated and purified by column chromatography to give the title compound.

Example 5

Compound of formula I: A and B taken together with the carbon atom to which they are attached are C=CHS(CH$_2$)$_2$-phenyl, L is CH$_2$CH$_3$, W is OCH$_3$, X and Y taken together with the carbon atom to which they are attached are C=O, Z is OH and R$_2$' is H.

Step 5a. Compound 1.6 of Scheme 1: R is —S(CH)$_2$)$_2$-phenyl, R$_{11}$ is H and R$_2$' is Bz.

A solution of the compound from Step 4a of Example 4 (200 mg, 0.18 mmol) in ethanol (5.0 mL) was treated with hydrochloric acid (2 M, 5.0 mL) at 60° C. for 2 hours before partition (ethyl acetate and saturated NaHCO$_3$). The organic phases were washed with water and brine, dried (Na$_2$SO$_4$) and evaporated. The residue was chromographed (silica, hexanes:acetone/95:5~85:15) to give the title compound (81.6 mg, 53%) as a 3:1 isomeric mixture.

MS (ESI) m/z=852 (M+H)$^+$.

Step 5b. Compound of formula I: A and B taken together with the carbon atom to which they are attached are C=CHS(CH$_2$)$_2$-phenyl, L is CH$_2$CH$_3$, W is OCH$_3$, X and Y taken together with the carbon atom to which they are attached are C=O, Z is OH and R$_2$' is H.

A solution of the compound from Step 5a in methanol is refluxed for 24 hours, evaporated and purified by column chromatography to give the title compound.

Example 6

Compound of formula II: A is H, B is —CH$_2$SC(O)CH$_3$, L is CH$_2$CH$_3$, W is OCH$_3$, X and Y taken together with the carbon atom to which they are attached are C=O, R$_4$" is Bz and R$_2$' is H.

Step 6a. Compound of formula 1.3 of Scheme 1: $R_2'$ is Bz, $R_4''$ is Bz and $R_{11}$ is H.

Into a mixture of the compound from Step 1a of Example 1 (30.25 g, 32.24 mmol), allyl (tert-butyl)carbonate (6.63 g, 41.92 mmol) and 1,4bis(diphenylphosphino)butane (931 mg, 2.18 mmol) in freshly distilled THF (200 ml) was added $Pd_2(dba)_3$ (1.000 g, 1.09 mmol). The reaction mixture was heated to reflux slowly. After refluxing for 16 hours, the mixture was cooled to room temperature and evaporated. The residue was purified by silica gel chromatography (hexanes:acetone/98:2~9:1) and recrystallization (acetonitrile) to give the title compound (28.31 g, 90%).

MS (ESI) m/z: 978 (M+H)$^+$.

$^{13}$C-NMR (125 MHz, CDCl$_3$): δ 205.1, 174.1, 165.5, 164.6, 139.5, 138.0, 134.2, 132.7, 131.8, 130.2, 129.2, 129.0, 127.7, 127.4, 115.5, 100.0, 95.5, 79.3, 78.3, 77.7, 76.7, 76.4, 76.2, 76.0, 72.2, 71.8, 67.0, 63.2, 63.0, 62.7, 50.1, 49.0, 44.6, 40.2, 39.1, 38.5, 37.6, 34.8, 31.0, 21.6, 21.1, 20.6, 20.5, 19.0, 17.7, 17.6, 15.7, 12.1, 9.7, 9.1.

Step 6b. Compound formula II: A is H, B is —CH$_2$SC(O)CH$_3$, L is CH$_2$CH$_3$, W is OCH$_3$, X and Y taken together with the carbon atom to which they are attached are C=O, $R_4''$ is Bz and $R_2'$ is Bz.

A solution of the compound from Step 6a (297 mg, 0.30 mmol) in anhydrous toluene (6.0 mL) was heated to gentle reflux with thiolacetic acid (0.10 mL, 1.40 mmol) in the presence of 2,2'-azobisisobutyronitrile (AIBN, 18.8 mg) for 7 hours before additional AIBN (2×10 mg) was added every 6~14 hours interval during a total of 25 hour reaction. It was evaporated and the residue was chromatographed (silica, hexanes-acetone/97:3~9:1) to give the title compound (254 mg, 79%) as a 2.5:1 isomeric mixture.

MS (ESI) m/z=1054 (M+H)$^+$.

Step 6c. Compound of formula II: A is H, B is —CH$_2$SC(O)CH$_3$, L is CH$_2$CH$_3$, W is OCH$_3$, X and Y taken together with the carbon atom to which they are attached are C=O, $R_4''$ is Bz and $R_2'$ is H.

A solution of the compound from Step 6b in methanol is refluxed for 24 hours, evaporated and purified by column and high performance liquid chromatography to give the title compound.

Example 7

Compound of formula I: A is H, B is —CH$_2$SC(O)CH$_3$, L is CH$_2$CH$_3$, W is OCH$_3$, X and Y taken together with the carbon atom to which they are attached are C=O, Z is OH and $R_2'$ is H.

Step 7a. Compound of formula I: A is H, B is —CH$_2$SC(O)CH$_3$, L is CH$_2$CH$_3$, W is OCH$_3$, X and Y taken together with the carbon atom to which they are attached are C=O, Z is OH and $R_2'$ is Bz.

A solution of the compound from Step 6b of Example 6 (253 mg, 0.24 mmol) in ethanol (5.0 mL) was treated with hydrochloric acid (2 M, 5.0 mL) at 60° C. for 1.5 hours before partition (ethyl acetate and saturated NaHCO$_3$). The organic phases were washed with water and brine, dried (Na$_2$SO$_4$) and evaporated. The residue was chromographed (silica, hexanes:acetone/95:5~85:15) to give the title compound (173.5 mg, 91%) as a 2.5:1 isomeric mixture.

MS (ESI) m/z=792 (M+H)$^+$.

Step 7b. Compound of formula I: A is H, B is —CH$_2$SC(O)CH$_3$, L is CH$_2$CH$_3$, W is OCH$_3$, X and Y taken together with the carbon atom to which they are attached are C=O, Z is OH and $R_2'$ is H.

A solution of the compound from Step 7a in methanol is refluxed for 24 hours, evaporated and purified by column and high performance liquid chromatography to give the title compound.

Example 8

Compound of formula I: A is H, B is —CH$_2$SCH$_2$-(4-pyridinyl), L is CH$_2$CH$_3$, W is OCH$_3$, X and Y taken together with the carbon atom to which they are attached are C=O, Z is OH and $R_2'$ is H.

Step 8a. Compound of formula I: A is H, B is —CH$_2$SH, L is CH$_2$CH$_3$, W is OCH$_3$, X and Y taken together with the carbon atom to which they are attached are C=O, Z is OH and $R_2'$ is Bz.

A solution of the compound from Step 7a of Example 7 (173.5 mg, 0.22 mmol) in isopropanol (5.0 mL) was treated with aqueous NaOH (10%, 1.0 mL) at room temperature for 6 hours before partition (ethyl acetate and saturated NaHCO$_3$). The organic phases were washed with water and brine, dried (Na$_2$SO$_4$) and evaporated. The residue was chromographed (silica, hexanes:acetone/95:5~85:15) to give the title compound (67.6 mg, 41%) as a 2.5:1 isomeric mixture.

MS (ESI) m/z=750 (M+H)$^+$.

Step 8b. Compound of formula I: A is H, B is —CH$_2$SCH$_2$-(4-pyridinyl), L is CH$_2$CH$_3$, W is OCH$_3$, X and Y taken together with the carbon atom to which they are attached are C=O, Z is OH and $R_2'$ is Bz.

A mixture of the compound from Step 8a, 4-(bromomethyl)pyridine hydrobromide, potassium carbonate in N,N-dimethylformaldehyde is stirred at room temperature for 16 hours before partition (ethyl acetate and saturated NaHCO$_3$). The organic phases are washed with water and brine, dried (Na$_2$SO$_4$), evaporated and chromatographed to give the title compound.

Step 8c. Compound of formula I: A is H, B is —CH$_2$SCH$_2$-(4-pyridinyl), L is CH$_2$CH$_3$, W is OCH$_3$, X and Y taken together with the carbon atom to which they are attached are C=O, Z is OH and $R_2'$ is H.

A solution of the compound from Step 8b in methanol is refluxed for 24 hours, evaporated and chromatographed by column and high performance liquid chromatography to give the title compound.

Example 9

Compound of formula I: A and B taken together with the carbon atom to which they are attached are C=CHS(CH$_2$)$_2$-phenyl, L is CH$_2$CH$_3$, W is OCH$_3$, X and Y taken together with the carbon atom to which they are attached are C=O, Z is OH and $R_2'$ is H.

Step 9a. Compound of formula III: $R_2'$ is Bz and Z is H.

A solution of the compound from Step 1b of Example 1 (1.132 g, 1.16 mmol) in ethanol (10 mL) was treated with hydrochloric acid (2 M, 10 mL) at 60° C. for 6 hours before partition (ethyl acetate and saturated NaHCO$_3$). The organic phases were washed with water and brine, dried (Na$_2$SO$_4$) and evaporated. The residue was chromographed (silica, hexanes:acetone/95:5~7:3) to give the title compound (595 mg, 72%).

MS (ESI) m/z=714 (M+H)$^+$.

$^{13}$C-NMR (125 MHz, CDCl$_3$): δ 206.7, 175.5, 165.5, 141.6, 136.7, 132.6, 130.6, 129.8, 128.1, 102.9, 88.1, 80.0, 79.9, 78.9, 76.6, 76.0, 74.0, 72.2, 69.2, 64.2, 51.5, 48.7, 43.9, 40.7, 37.6, 37.3, 36.9, 30.7, 21.1, 20.2, 19.7, 17.2, 14.5, 13.0, 10.1, 9.9.

Step 9b. Compound 1.6 of Scheme 1: R is —S(CH$_2$)$_2$-phenyl, $R_{11}$ is H and $R_2'$ is Bz.

A solution of the compound from Step 9a in anhydrous toluene is heated to reflux with 2-phenylethylthiol in the presence of AIBN for 3 days according to the procedure described in Step 4a of Example 4. The solution is evaporated and chromatographed to give the title compound.

Step 9c. Compound of formula I: A and B taken together with the carbon atom to which they are attached are C=CHS(CH$_2$)$_2$-phenyl, L is CH$_2$CH$_3$, W is OCH$_3$, X and Y taken together with the carbon atom to which they are attached are C=O, Z is OH and R$_2$' is H.

A solution of the compound of Step 9b in methanol is refluxed for 24 hours, evaporated and purified by column and high performance liquid chromatography to give the title compound.

Example 10

Compound of formula I: A and B taken together with the carbon atom to which they are attached are C=CHSC(O)CH$_3$, L is CH$_2$CH$_3$, W is OCH$_3$, X and Y taken together with the carbon atom to which they are attached are C=O, Z is OH and R$_2$' is H.

Step 10a. Compound 1.6 of Scheme 1: R is —SC(O)CH$_3$, R$_{11}$ is H and R$_2$' is Bz.

A solution of the compound from Step 9a of Example 9 (505 mg, 0.71 mmol) in anhydrous toluene (14.0 mL) was heated to gentle reflux with thiolacetic acid (0.25 mL, 3.50 mmol) in the presence of 2,2'-azobisisobutyronitrile (AIBN, 22.7 mg) for 8 hours before additional AIBN (2×22 mg) was added every 6~14 hours interval during a total of 30 hour reaction. It was evaporated and the residue was chromatographed (silica, hexanes:acetone/95:5~4:1) to give the title compound (307 mg, 55%).

MS (ESI) m/z=790 (M+H)$^+$.

Step 10b. Compound of formula I: A and B taken together with the carbon atom to which they are attached are C=CHSC(O)CH$_3$, L is CH$_2$CH$_3$, W is OCH$_3$, X and Y taken together with the carbon atom to which they are attached are C=O, Z is OH and R$_2$' is H.

A solution of the compound from Step 10a in methanol is refluxed for 24 hours, evaporated and purified by column and high performance liquid chromatography to give the title compound.

Example 11

Compound of formula II: A and B taken together with the carbon atom to which they are attached are C=CHSCH$_2$-phenyl, L is CH$_2$CH$_3$, W is OCH$_3$, X and Y taken together with the carbon atom to which they are attached are C=O, R$_4$" is Bz and R$_2$' is H.

Step 11a. Compound 1.1 of Scheme 1: R$_2$ is H, R$_2$' is H and R$_4$" is Bz.

A solution of the compound from Step 1a of Example 1 (5.50 g, 4.80 mmol) in MeOH (200 mL) was refluxed for 16 hours before evaporation. The residue was chromatographed (silica, hexanes:acetone) to give the the title compound (4.85 g, 99%).

MS (ESI) m/z=834 (M+H)$^+$.

$^{13}$C-NMR (125 MHz, CDCl$_3$): δ 205.6, 184.5, 177.7, 171.5, 167.5, 153.4, 139.5, 135.4, 129.6, 127.6, 127.32, 127.0, 102.8, 79.1, 78.9, 76.5, 75.3, 74.4, 70.2, 69.5, 65.8, 62.9, 62.7, 50.5, 46.0, 40.2, 38.5, 28.3, 25.1, 23.6, 21.2, 20.0, 19.2, 17.5, 14.9, 13.8, 13.4, 12.6.

Step 11b. Compound 1.1 of Scheme 1: R$_2$ is H, R$_2$' is triethylsilyl and R$_4$" is Bz.

A solution of the compound from Step 11a (4.87 g, 5.85 mmol), imidazole (2.39 g, 35.14 mmol) and DMAP (150 mg, 1.23 mmol) in DMF (20 mL) was treated with triethylsilyl chloride (1.13 mL, 6.73 mmol) at room temperature for 10 hours. The reaction mixture was diluted with ethyl acetate (200 mL), washed with water and brine, dried and concentrated. The crude residue was purified by chromatography (silica, hexanes:acetone/20:1~3:1) to give the title compound (5.73 g, 78%).

MS (ESI) m/z=948 (M+H)$^+$.

$^{13}$C-NMR (125 MHz, CDCl$_3$): δ 207.7, 175.3, 166.3, 142.2, 133.2, 129.9, 128.3, 103.1, 96.3, 79.1, 78.4, 73.4, 73.0, 72.7, 67.5, 66.1, 63.4, 50.9, 49.6, 45.2, 41.1, 40.8, 40.5, 35.6, 31.6, 29.3, 22.1, 20.7, 18.4, 14.1, 13.3, 10.6, 7.0, 5.1.

Step 11c. Compound 1.2 of Scheme 1: R$_{11}$ is H, R$_2$' is triethylsilyl and R$_4$" is Bz.

Into a suspension of the compound from Step 11b (3.25 g, 3.43 mmol), tetrabutylammonium iodide (253 mg, 0.69 mmol) and 50% NaOH aqueous solution (20 mL) in methylene chloride (20 mL) was added propargyl bromide (80% solution in toluene, 1.31 mL, 13.72 mmol) at room temperature. The mixture was stirred vigorously for 18 hours, diluted with ethyl acetate (200 mL), washed with water and brine, dried (Na$_2$SO$_4$) and concentrated. The crude residue was purified by chromatography (silica, hexanes:acetone/20:1) to give the title compound (2.09 g, 62%).

MS (ESI) m/z=986 (M+H)$^+$.

$^{13}$C-NMR (125 MHz, CDCl$_3$): δ 207.5, 174.9, 166.3, 138.3, 133.2, 129.9, 129.8, 128.3, 102.4, 96.7, 80.1, 79.2, 79.0, 78.1, 76.3, 74.0, 73.1, 72.7, 67.5, 66.0, 63.3, 51.5, 51.1, 49.6, 45.6, 39.8, 35.7, 31.6, 29.3, 23.1, 22.6, 21.6, 21.2, 19.8, 18.5, 14.1, 12.7, 10.3, 7.0, 5.1.

Step 11d. Compound of formula II: A and B taken together with the carbon atom to which they are attached are C=CHSCH$_2$-phenyl, L is CH$_2$CH$_3$, W is OCH$_3$, X and Y taken together with the carbon atom to which they are attached are C=O, R$_4$" is Bz and R$_2$' is triethylsilyl.

A solution of the compound from Step 11c (200 mg, 0.20 mmol) in toluene (5.0 mL) containing AIBN (3.3 mg, 0.02 mmol) and benzyl mercaptan (0.048 mL, 0.40 mmol) was refluxed for 10 hours. Removal of the solvent by evaporation gave the crude title compound (221 mg).

MS (ESI) m/z=1110 (M+H)$^+$.

Step 11e. Compound of formula II: A and B taken together with the carbon atom to which they are attached are C=CHSCH$_2$-phenyl, L is CH$_2$CH$_3$, W is OCH$_3$, X and Y taken together with the carbon atom to which they are attached are C=O, R$_4$" is Bz and R$_2$' is H.

A solution of the compound from Step 11d in THF is treated with tetrabutylammonium fluoride at room temperature for 2 hours. Removal of the solvent gives the title compound.

Example 12

Compound of formula II: A and B taken together with the carbon atom to which they are attached are C=O, L is CH$_2$CH$_3$, W is OCH$_3$, X and Y taken together with the carbon atom to which they are attached are C=O, R$_4$" is Bz and R$_2$' is H.

Step 12a. Compound 1.1 of Scheme 1: R$_2$ is CH$_2$CH(OH)CH$_2$OH, R$_2$' is Bz and R$_4$" is Bz.

A solution of the compound from Step 6a of Example 6 (1.40 g, 1.43 mmol), 4-methylmorpholine N-oxide (503 mg, 4.29 mmol), OsO$_4$ (4 wt % in water, 1.52 mL) in THF (30 mL) and water (7.5 mL) was refluxed overnight, diluted with methylene chloride, washed with saturated NaHCO$_3$ and brine, dried (Na$_2$SO$_4$) and concentrated. The residue was purified by chromatography (silica, hexanes:acetone/2:1) to give the title compound (681 mg, 47%).

MS (ESI) m/z=1012 (M+H)$^+$.

Step 12b Compound 1.1 of Scheme 1: R$_2$ is CH$_2$CHO, R$_2$' is Bz and R$_4$' is Bz.

A mixture of the compound from Step 12a (390 mg, 0.39 mmol) and NaIO$_4$ (82 mg, 0.78 mmol) in THF (6.7 mL) and water (1.6 mL) was stirred at room temperature for 2 hours, diluted with ethyl acetate (50 mL), washed with water (×3) and brine, dried (Na$_2$SO$_4$) and concentrated to give the crude title compound (289 mg, 83%).

MS (ESI) m/z=980 (M+H)$^+$.

Step 12c. Compound of formula II: A is H, B is OH, X and Y taken together with the carbon to which they are attached are C=O, R$_2$' is Bz, and R$_4$" is Bz.

To a solution of $CH_2I_2$ (0.048 mL) in THF (1.5 mL) was added Sm (samarium) powder (98 mg) at room temperature. The mixture was stirred at 35° C. until the Sm powder disappeared. Then a solution of the compound from Step 12b (58 mg, 0.059 mmol) in THF (59 mL) was introduced dropwise. After 10 minutes, the reaction was quenched by water (4 mL) and extracted with EtOAc. The extracts were washed with water and brine, dried ($Na_2SO_4$) and concentrated. The residue was purified by chromatography (silica, hexanes:acetone/2:1) to give the title compound (29 mg, 50%).

MS (ESI) m/z=982 (M+H)$^+$.

Step 12d. Compound of formula II: A and B taken together with the carbon atom to which they are attached are C=O, L is $CH_2CH_3$, W is $OCH_3$, X and Y taken together with the carbon atom to which they are attached are C=O, $R_4''$ is Bz and $R_2'$ is Bz.

A solution of the compound from Step 12c (28 mg, 0.029 mmol) in methylene chloride (0.5 mL) was treated with Dess-Martin periodinane (30 mg, 0.041 mmol) for 40 minutes at room temperature. Evaporation and purification by chromatography (silica, hexanes:acetone/4:1) gave the title compound (19 mg, 68%).

MS (ESI) m/z=980 (M+H)$^+$.

Step 12e. Compound of formula I: A and B taken together with the carbon atom to which they are attached are C=O, L is $CH_2CH_3$, W is $OCH_3$, X and Y taken together with the carbon atom to which they are attached are C=O, $R_4''$ is Bz and $R_2'$ is H.

A solution of the compound from Step 12d in methanol is stirred at 55° C. for 24 hours, evaporated and purified by column and high performance liquid chromatography to give the title compound.

Example 13

Compound of formula II: A is H, B is OH, X and Y taken together with the carbon to which they are attached are C=O, $R_2'$ is H, and $R_4''$ is H.

A solution of the compound from Step 12c in methanol is stirred at 55° C. for 24 hours, evaporated and purified by column and high performance liquid chromatography to give the title compound.

Although the invention has been described in detail with respect to various preferred embodiments it is not intended to be limited thereto, but rather those skilled in the art will recognize that variations and modifications may be made therein which are within the spirit of the invention and the scope of the appended claims.

What is claimed is:

1. A compound represented by the formula

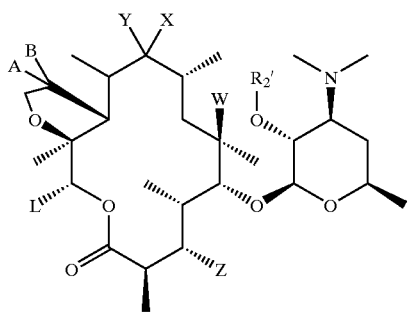

(I)

or a pharmaceutically acceptable salt, ester or prodrug thereof
wherein

A is selected from:
(a) —OH;
(b) —$OR_p$, where $R_p$ is a hydroxy protecting group,
(c) —$R_1$, where $R_1$ is selected from:
  1. aryl;
  2. substituted aryl;
  3. heteroaryl; and
  4. substituted heteroaryl;
(d) —$OR_1$, where $R_1$ is as previously defined;
(e) —$R_2$, where $R_2$ is selected from:
  1. hydrogen;
  2. halogen;
  3. $C_1$–$C_6$ alkyl containing 0, 1, 2, or 3 heteroatoms selected from O, S and N, optionally substituted with one or more substituents selected from halogen, cyano, oxo, aryl, substituted aryl, heteroaryl and substituted heteroaryl;
  4. $C_2$–$C_6$ alkenyl containing 0, 1, 2, or 3 heteroatoms selected from O, S and N, optionally substituted with one or more substituents selected from halogen, cyano, oxo, aryl, substituted aryl, heteroaryl and substituted heteroaryl; and
  5. $C_2$–$C_6$ alkynyl containing 0, 1, 2, or 3 heteroatoms selected from O, S and N, optionally substituted with one or more substituents selected from halogen, cyano, oxo, aryl, substituted aryl, heteroaryl and substituted heteroaryl;
(f) —$OR_2$, where $R_2$ is previously defined;
(g) —$S(O)_nR_{11}$, where n=0, 1 or 2, and $R_{11}$ is selected from hydrogen, $R_1$ and $R_2$, where $R_1$ and $R_2$ are as previously defined
(h) —$OC(O)R_{11}$, where $R_{11}$ is as previously defined:
(i) —$C(O)R_{11}$, where $R_{11}$ is as previously defined;
(j) —$C(O)NHR_{11}$, where $R_{11}$ is as previously defined;
(k) —$OC(O)NHR_{11}$, where $R_{11}$ is as previously defined;
(l) —$NHC(O)R_{11}$, where $R_{11}$ is as previously defined;
(m) —$NHC(O)NHR_{11}$, where $R_{11}$ is as previously defined;
(n) —$NHS(O)_nR_{11}$, where n and $R_{11}$ are as previously defined;
(o) —$NR_{14}R_{15}$, where $R_{14}$ and $R_{15}$ are each independently $R_{11}$, where $R_{11}$ is as previously defined; and
(p) —$NHR_3$, where $R_3$ is an amino protecting group;

B is selected from:
(a) hydrogen;
(b) deuterium;
(c) —CN;
(d) —$NO_2$;
(e) halogen;
(f) —OH;
(g) —$R_1$, where $R_1$ is as previously defined;
(h) —$R_2$, where $R_2$ is as previously defined; and
(i) —$OR_p$, where $R_p$ is as previously defined;
provided that when B is halogen, —$NO_2$, —OH or $OR_p$, A is $R_1$ or $R_2$;
or, alternatively, A and B taken together with the carbon atom to which they are attached are selected from:
(a) C=O;
(b) $C(OR_2)_2$, where $R_2$ is as previously defined;
(c) $C(SR_2)_2$, where $R_2$ is as previously defined;
(d) $C(OR_{12})(OR_{13})$, where $R_{12}$ and $R_{13}$ taken together are —$(CH_2)_m$—, and where m is 2 or 3;

(e) C(SR$_{12}$)(SR$_{13}$), where R$_{12}$ and R$_{13}$ taken together are —(CH$_2$)$_m$— and, where m is as previously defined,
(f) C=CR$_{11}$R$_{14}$, where R$_{11}$ and R$_{14}$ are as previously defined;
(g) C=N—O—R$_{11}$, where R$_{11}$ is as previously defined;
(h) C=NNHR$_{11}$, where R$_{11}$ is as previously defined;
(i) C=NNHC(O)R$_{11}$, where R$_{11}$ is as previously defined;
(j) C=NN=CR$_{11}$R$_{14}$, where R$_{11}$ and R$_{14}$ are as previously defined;
(k) C=NNHC(O)NMR$_{11}$, where R$_{11}$ is as previously defined;
(l) C=NNHS(O)$_n$R$_{11}$, where n and R$_{11}$ are as previously defined;
(m) C=NNHR$_3$, where R$_3$ is as previously defined; and
(n) C=NR$_{11}$, where R$_{11}$ is as previously defined;

one of X and Y is hydrogen and the other is selected from:
(a) hydrogen;
(b) deuterium;
(c) —OH;
(d) —OR$_p$, where R$_p$ is as previously defined; and
(e) —NR$_4$R$_5$, where R$_4$ and R$_5$ are each independently selected from:
  1. hydrogen; and
  2. C$_1$–C$_{12}$ alkyl, optionally substituted with one or more substituents selected from halogen, cyano, aryl, substituted aryl, heteroaryl and substituted heteroaryl; or
 R$_4$ and R$_5$, taken together with the nitrogen atom to which they are attached form a 3–10 membered heteroalkyl ring containing 0–2 additional hetero atoms selected from O, S and N; or alternatively, X and Y taken together with the carbon atom to which they are attached are selected from:
(a) C=O;
(b) C=NR$_{11}$, where R$_{11}$ is as previously defined;
(c) C=NC(O)R$_{11}$, where R$_{11}$ is as previously defined;
(d) C=N—OR$_6$, where R$_6$ is selected from:
  1. hydrogen;
  2. —CH$_2$O(CH$_2$)$_2$OCH$_3$,
  3. —CH$_2$O(CH$_2$O)$_n$CH$_3$, where n is as previously defined;
  4. —C$_1$–C$_{12}$ alkyl, optionally substituted with one or more substituents selected from halogen, cyano, aryl, substituted aryl, heteroaryl and substituted heteroaryl;
  5. C$_3$–C$_{12}$ cycloalkyl;
  6. C(O)—C$_1$–C$_{12}$ alkyl;
  7. C(O)—C$_3$–C$_{12}$ cycloalkyl;
  8. C(O)—R$_1$, where R$_1$ is as previously defined; and
  9. —Si(R$_a$)(R$_b$)(R$_c$), wherein R$_a$, R$_b$ and R$_c$ are each independently selected from C$_1$–C$_{12}$ alkyl, aryl and substituted aryl; and
(e) C=N—O—C(R$_7$)(R$_8$)—O—R$_6$, where R$_6$ is as previously defined, provided that R$_6$ is not C(O)—C$_1$–C$_{12}$ alkyl, C(O)—C$_3$–C$_{12}$ cycloalkyl, or C(O)—R$_1$; and R$_7$ and R$_8$ taken together with the carbon atom to which they are attached form a C$_3$–C$_{12}$ cycloalkyl group or each is independently selected from:
  1. hydrogen: and
  2. C$_1$–C$_{12}$ alkyl;

L is selected form:
(a) —CH(OH)CH$_3$;
(b) C$_1$–C$_6$ alkyl, optionally substituted with one or more substituents selected from halogen, cyano, aryl, substituted aryl, heteroaryl and substituted heteroaryl;
(c) C$_2$–C$_6$ alkenyl, optionally substituted with one or more substituents selected from halogen, cyano, aryl, substituted aryl, heteroaryl and substituted heteroaryl; and
(d) C$_2$–C$_6$ alkynyl, optionally substituted with one or more substituents selected from halogen, cyano, aryl, substituted aryl, heteroaryl and substituted heteroaryl;

W is selected from:
(a) hydrogen;
(b) —OH;
(c) —CN;
(d) —OR$_{10}$, where R$_{10}$ is methyl, optionally substituted with one or more substituents selected from:
  1. halogen;
  2. deuterium;
  3. —CN;
  4. —R$_1$, where R$_1$ is as previously defined;
  5. —OR$_{11}$, where R$_{11}$ is as previously defined;
  6. —S(O)$_n$R$_{11}$, where n and R$_{11}$ are as previously defined;
  7. —OC(O)R$_{11}$, where R$_{11}$ is as previously defined;
  8. —C(O)R$_{11}$, where R$_{11}$ is as previously defined;
  9. —C(O)OR$_{11}$, where R$_{11}$ is as previously defined;
  10. —C(O)NHR$_{11}$, where R$_{11}$ is as previously defined;
  11. —OC(O)NHR$_{11}$, where R$_{11}$ is as previously defined;
  12. —NHC(O)R$_{11}$, where R$_{11}$ is as previously defined;
  13. —NHC(O)NHR$_{11}$, where R$_{11}$ is as previously defined; and
  14. —NHS(O)$_n$R$_{11}$, where n and R$_{11}$ are as previously defined; and
(e) —OC(O)NHR$_{11}$, where R$_{11}$ is as previously defined;

Z is selected from:
(a) hydrogen;
(b) —OH;
(c) —OR$_p$, where R$_p$ is as previously defined;
(d) —OR$_{11}$, where R$_{11}$ is as previously defined;
(e) —OC(O)R$_{11}$, where R$_{11}$ is as previously defined;
(f) —OC(O)NHR$_{11}$, where R$_{11}$ is as previously defined,
(g) —S(O)$_n$R$_{11}$, where n and R$_{11}$ are as previously defined;
(h) —

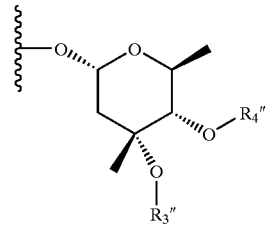

where R$_3$" is hydrogen or methyl: R$_4$" is hydrogen or R$_p$, where R$_p$ is as previously defined; and R$_2$' is hydrogen or R$_p$, where R$_p$, is as previously defined.

2. A compound according to claim 1 which is represented by the formula

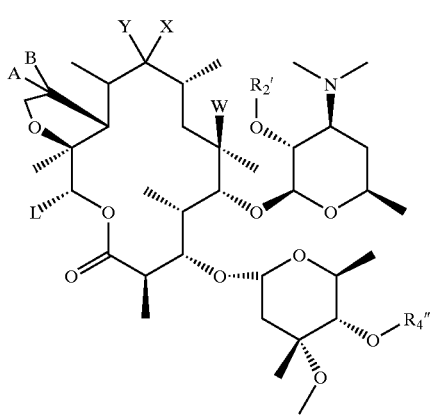

(II)

wherein A, B, L, W, X, Y, $R_2'$ and $R_4''$ are as defined in claim 1.

3. A compound according to claim 1 wherein L is ethyl and A, B, W, X, Y, Z and $R_2'$ are as defined in claim 1.

4. A compound according to claim 3 wherein W is —$OCH_3$, and X and Y taken together with the carbon atom to which they are attached are C=O.

5. A compound according to claims 1 or 2 which is selected from:

Compound of formula II: A and B taken together with the carbon atom to which they are attached are C=$CH_2$, L is $CH_2CH_3$, W is $OCH_3$, X and Y taken together with the carbon atom to which they are attached are C=O, $R_4''$ is Bz and $R_2'$ is H;

Compound of formula II: A and B taken together with the carbon atom to which they are attached are C=$CH_2$, L is $CH_2CH_3$, W is $OCH_3$, X and Y taken together with the carbon atom to which they are attached are C=O, $R_4''$ is H and $R_2'$ is H;

Compound of formula I: A and B taken together with the carbon atom to which they are attached are C=$CH_2$, L is $CH_2CH_3$, W is $OCH_3$, X and Y taken together with the carbon atom to which they are attached are C=O, Z is OH and $R_2'$ is H;

Compound of formula II: A and B taken together with the carbon atom to which they attached are C=CHS($CH_2$)$_2$-phenyl, L is $CH_2CH_3$, W is $OCH_3$, X and Y taken together with the carbon atom to which they attached are C=O, $R_4''$ is Bz and $R_2'$ is H;

Compound of formula I: A and B taken together with the carbon atom to which they are attached are C=CHS($CH_2$)$_2$-phenyl, L is $CH_2CH_3$, W is $OCH_3$, X and Y taken together with the carbon atom to which they are attached are C=O, Z is OH and $R_2'$ is H;

Compound of formula II: A is H, B is —$CH_2SC(O)CH_3$, L is $CH_2CH_3$, W is $OCH_3$, X and Y taken together with the carbon atom to which they are attached are C=O, $R_4''$ is Bz and $R_2'$ is H;

Compound of formula I: Compound of formula I: A is H, B is —$CH_2SC(O)CH_3$, L is $CH_2CH_3$, W is $OCH_3$, X and Y taken together with the carbon atom to which they are attached are C=O, Z is OH and $R_2'$ is H;

Compound of formula I: A is H, B is —$CH_2SCH_2$-(4-pyridyl), L is $CH_2CH_3$, W is $OCH_3$, X and Y taken together with the carbon atom to which they are attached are C=O, Z is OH and $R_2'$ is H;

Compound of formula I: A and B taken together with the carbon atom to which they attached are C=CHS($CH_2$)$_2$-phenyl, L is $CH_2CH_3$, W is $OCH_3$, X and Y taken together with the carbon atom to which they attached are C=O, Z is OH and $R_2'$ is H;

Compound of formula I: A and B taken together with the carbon atom to which they are attached are C=CHSC(O)$CH_3$, L is $CH_2CH_3$, W is $OCH_3$, X and Y taken together with the carbon atom to which they are attached are C=O, Z is OH and $R_2'$ is H;

Compound of formula II: A and B taken together with the carbon atom to which they are attached are C=CHS$CH_2$-phenyl, L is $CH_2CH_3$, W is $OCH_3$, X and Y taken together with the carbon atom to which they are attached are C=O, $R_4$ is Bz and $R_2'$ is H;

Compound of formula II: A and B taken together with the carbon atom to which they are attached are C=O, L is $CH_2CH_3$, W is $OCH_3$, X and Y taken together with the carbon atom to which they are attached are C=O, $R_4$ is Bz and $R_2'$ is H;

Compound of formula II: A is H, B is OH, X and Y taken together with the carbon atom to which they are attached are C=O, $R_2'$ is H, and $R_4''$ is H.

6. A pharmaceutical composition comprising a therapeutically effective amount of a compound of claim 1, or a pharmaceutically-acceptable salt, ester or prodrug thereof, in combination with a pharmaceutically acceptable carrier.

7. A method for controlling a bacterial infection in a subject comprising administering to a subject a therapeutically-effective amount of a pharmaceutical composition according to claim 6.

8. A method for the preparation of a compound of Formula I as defined in claim 1 wherein A and B taken together with the carbon atom to which they are attached are C=$CR_{11}R_{14}$, comprising the step of:

i) reacting a compound represented by the formula

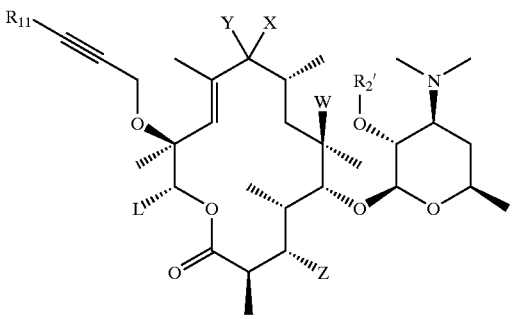

where $R_2'$, X, Y, W, Z, L, and $R_{11}$ are as defined in claim 1, with a radical species in the presence of 2,2'-axobisisobutyronitrile, optionally in the presence of a reducing agent in an aprotic solvent at from about 40° C. to about 150° C. for from 1 hour to 10 days to provide a compound of Formula I, wherein A and B taken together with the carbon atom to which they are attached are C=$CR_{11}R_{14}$.

9. A method for preparing a compound of formula I as defined in claim 1, where A is hydrogen and B is —$CHR_{11}R_{14}$, comprising the step of:

i) reacting a compound represented by the formula

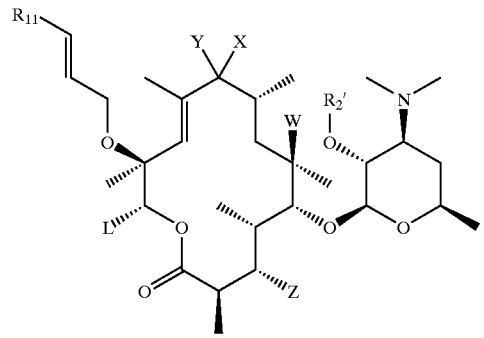

where L, W, X, Y, Z, $R_2'$, and $R_{11}$ are as defined in claim 1, with a radical species in the presence of 2,2'-azobisisobutyronitrile, optionally in the presence of a reducing agent in an aprotic solvent at from about 40° C. to about 150° C. for from 1 hour to 10 days to provide a compound of Formula I, wherein A is hydrogen, B is —$CHR_{11}R_{14}$.

* * * * *